US009951766B2

United States Patent
Akita et al.

(10) Patent No.: US 9,951,766 B2
(45) Date of Patent: Apr. 24, 2018

(54) PRESSURE DETECTION DEVICE OF LIQUID FLOW ROUTE

(71) Applicant: Nikkiso Company Limited, Tokyo (JP)

(72) Inventors: Kunihiko Akita, Shizuoka (JP); Sumiaki Matsuo, Shizuoka (JP)

(73) Assignee: NIKKISO COMPANY LIMITED, Tokyo (JP)

( * ) Notice: Subject to any disclaimer, the term of this patent is extended or adjusted under 35 U.S.C. 154(b) by 446 days.

(21) Appl. No.: 14/688,068

(22) Filed: Apr. 16, 2015

(65) Prior Publication Data

US 2015/0238677 A1 Aug. 27, 2015

Related U.S. Application Data

(63) Continuation of application No. PCT/JP2013/078271, filed on Oct. 18, 2013.

(30) Foreign Application Priority Data

Oct. 19, 2012 (JP) ................ 2012-231969

(51) Int. Cl.
  *F04B 43/12* (2006.01)
  *A61M 1/36* (2006.01)
  (Continued)

(52) U.S. Cl.
  CPC ........ *F04B 43/1253* (2013.01); *A61B 5/6866* (2013.01); *A61M 1/1603* (2014.02);
  (Continued)

(58) Field of Classification Search
  CPC .............. F04B 43/1253; F04B 2205/01; F04B 2205/02; F04B 2205/03; F04B 2205/04; F04B 2205/05; F04B 2205/06
  See application file for complete search history.

(56) References Cited

U.S. PATENT DOCUMENTS 3,046,788 A 7/1962 Laimins
4,090,404 A 5/1978 Dupont
(Continued)

FOREIGN PATENT DOCUMENTS

EP 1666078 6/2006
EP 2749858 7/2014
(Continued)

OTHER PUBLICATIONS

International Search Report, Application No. PCT/JP2013/078271, dated Jan. 21, 2014.
(Continued)

*Primary Examiner* — Patrick Hamo
(74) *Attorney, Agent, or Firm* — The Dobrusin Law Firm, P.C.

(57) ABSTRACT

A pressure detection device of a liquid flow route includes; displacement detecting means that detects displacement of a peristaltically-actuated tube in the radial direction; pressure calculating means that is able to calculate blood removal pressure based on the displacement of the peristaltically-actuated tube; closed flow route forming means that is able to form a closed flow route which includes a portion at which the displacement detecting means is disposed; pressure changing means that is able to arbitrarily change the pressure in the closed flow route; pressure detection means that is able to detect pressure change in the closed flow route; and calibration curve acquiring means that is able to produce and acquire a calibration curve with which the displacement detecting means and the pressure calculating means are calibrated by a relationship between the pressure change detected by the pressure detection means and a detection value of the displacement detecting means.

20 Claims, 13 Drawing Sheets

(51) Int. Cl.
  *A61B 5/00*   (2006.01)
  *F04B 43/00*  (2006.01)
  *A61M 1/16*   (2006.01)
  *A61M 1/26*   (2006.01)
  *A61M 1/10*   (2006.01)

(52) U.S. Cl.
  CPC .......... *A61M 1/267* (2014.02); *A61M 1/3639* (2013.01); *F04B 43/0081* (2013.01); *A61B 2562/0247* (2013.01); *A61M 1/1006* (2014.02); *A61M 1/1039* (2014.02); *A61M 1/1086* (2013.01); *A61M 2205/3355* (2013.01); *A61M 2205/702* (2013.01); *F04B 2205/01* (2013.01); *F04B 2205/02* (2013.01); *F04B 2205/03* (2013.01); *F04B 2205/04* (2013.01)

(56) References Cited

U.S. PATENT DOCUMENTS

| | | | |
|---|---|---|---|
| 4,460,355 | A | 7/1984 | Layman |
| 4,498,843 | A | 2/1985 | Schneider |
| 4,534,756 | A | 8/1985 | Nelson |
| 4,743,228 | A | 5/1988 | Butterfiedl |
| 4,762,518 | A | 8/1988 | Kreinick |
| 4,784,576 | A | 11/1988 | Bloom |
| 4,969,808 | A | 11/1990 | Tsukada |
| 5,024,099 | A | 6/1991 | Lee |
| 5,215,450 | A | 6/1993 | Tamari |
| 5,336,051 | A * | 8/1994 | Tamari ............... A61M 1/3621 417/19 |
| 5,356,378 | A | 10/1994 | Doan |
| 5,380,172 | A | 1/1995 | Ulbing |
| 5,429,783 | A | 7/1995 | Tamari |
| 5,720,721 | A | 2/1998 | Dumas et al. |
| 5,813,842 | A | 9/1998 | Tamari |
| 5,814,004 | A | 9/1998 | Tamari |
| 5,920,054 | A * | 7/1999 | Uber, III ............... A61M 5/172 235/375 |
| 5,927,951 | A * | 7/1999 | Tamari ............... A61M 1/3639 417/476 |
| 6,039,078 | A | 3/2000 | Tamari |
| 6,374,084 | B1 * | 4/2002 | Fok ............... H04B 17/0085 324/601 |
| 6,497,680 | B1 * | 12/2002 | Holst ............... A61M 5/14224 604/153 |
| 6,868,720 | B2 * | 3/2005 | Lobdell ............... A61M 1/0031 600/488 |
| 7,004,924 | B1 | 2/2006 | Brugger |
| 7,037,092 | B2 | 5/2006 | Kagawa |
| 7,462,163 | B2 | 12/2008 | Yap |
| 7,935,912 | B2 | 5/2011 | Arima |
| 8,011,905 | B2 * | 9/2011 | Artsyukhovich ... A61M 1/0058 417/474 |
| 9,004,886 | B2 | 4/2015 | Beck |
| 9,662,433 | B2 * | 5/2017 | Matsuo ............... F04B 43/1261 |
| 2002/0151838 | A1 | 10/2002 | Beck et al. |
| 2003/0214412 | A1 | 11/2003 | Ho |
| 2008/0154095 | A1 | 6/2008 | Stubkjaer |
| 2010/0049134 | A1 | 2/2010 | Schuman, Jr. |
| 2010/0106466 | A1 | 4/2010 | Frohlich |
| 2010/0203179 | A1 | 8/2010 | Kaushik |
| 2011/0230814 | A1 | 9/2011 | Kopperschmidt et al. |
| 2012/0082576 | A1 | 4/2012 | Beck |
| 2014/0219829 | A1 | 8/2014 | Matsuo et al. |

FOREIGN PATENT DOCUMENTS

| | | |
|---|---|---|
| JP | S56-113083 A | 9/1981 |
| JP | S64-022357 | 2/1989 |
| JP | 03-001290 | 1/1991 |
| JP | H03-001290 | 1/1991 |
| JP | H04-015938 | 2/1992 |
| JP | H08-510812 A | 11/1996 |
| JP | 2003-265601 A | 9/2003 |
| JP | 2004-049494 | 2/2004 |
| JP | 2004-187990 | 7/2004 |
| JP | 2008-000425 A | 1/2008 |
| JP | 2008-002388 A | 1/2008 |
| JP | 2008-208808 | 9/2008 |
| JP | 2008-289635 A | 12/2008 |
| JP | 2009-525770 | 7/2009 |
| JP | 2010-188170 A | 9/2010 |
| JP | 2011-030880 A | 2/2011 |
| JP | 2012-192100 A | 10/2012 |
| WO | WO1994/028309 | 8/1994 |
| WO | WO 9428309 A1 * | 12/1994 .......... A61M 1/3621 |
| WO | 9710013 | 3/1997 |
| WO | 2007/093064 A1 | 8/2007 |
| WO | 2010/020380 A1 | 2/2010 |

OTHER PUBLICATIONS

Potentially Related U.S. Appl. No. 14/186,193, published as 2014/0219829, published on Aug. 7, 2014.
International Search Report, Application No. PCT/JP2013/078272, dated Jan. 21, 2014.
Supplementary European Search Report dated May 27, 2016 for Application No. PCT/JP2013078272.
Translation of International Search Report, Application No. PCT/JP2012/070614, dated Sep. 11, 2012.
Extended European Search Report dated Apr. 8, 2015 for Application No. 12826289.

* cited by examiner

[Fig 1]
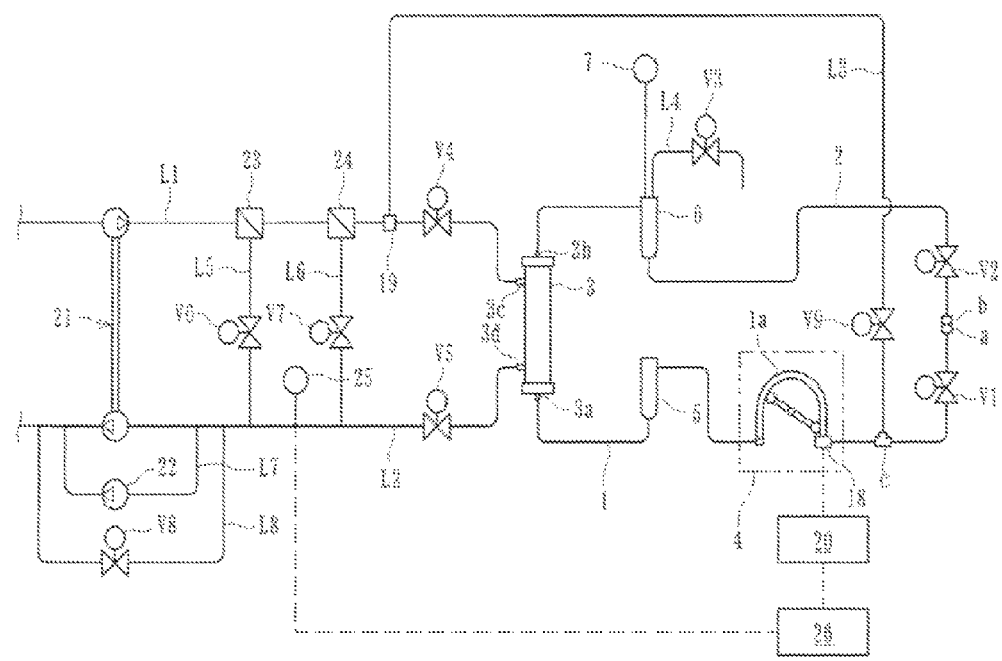

[Fig 2]
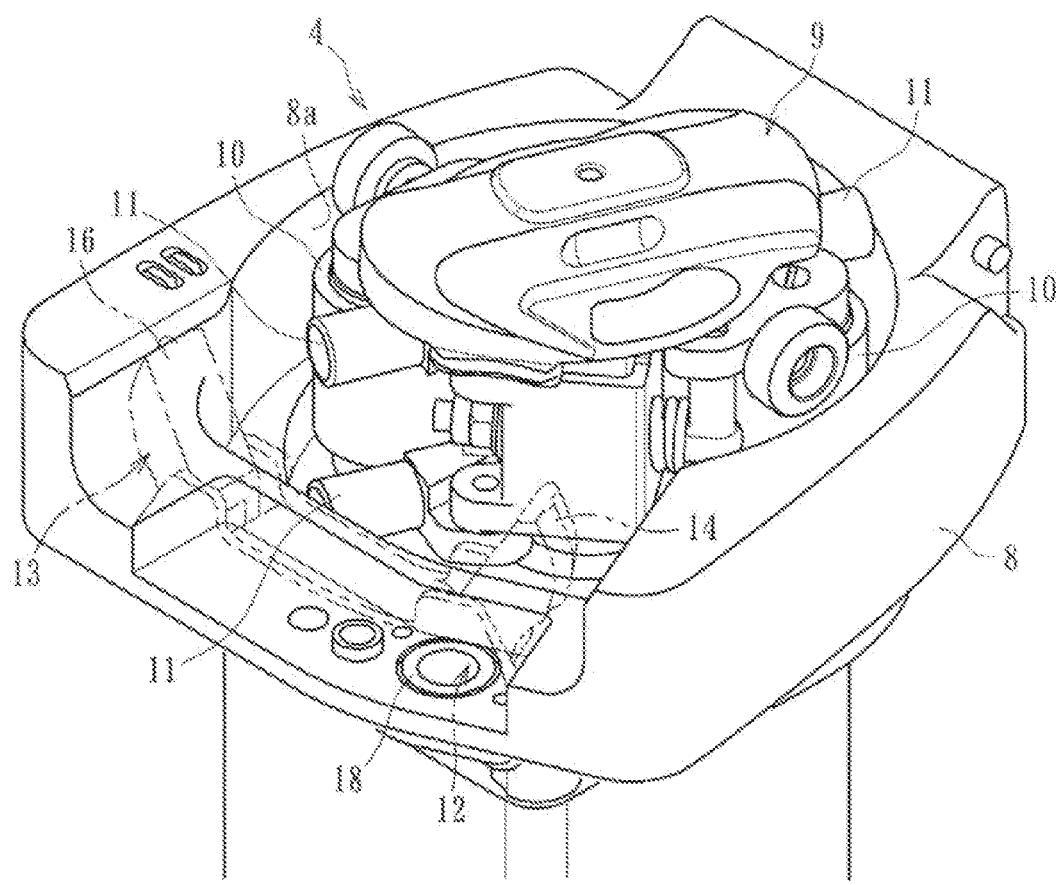

[Fig 3]
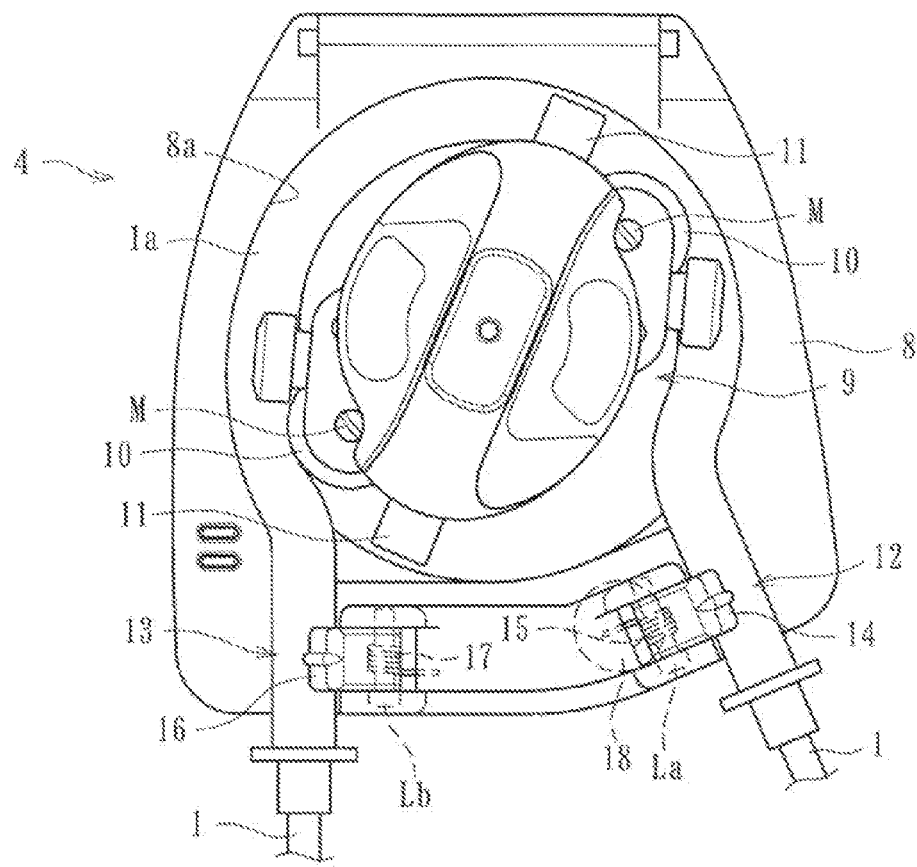
[Fig 4]
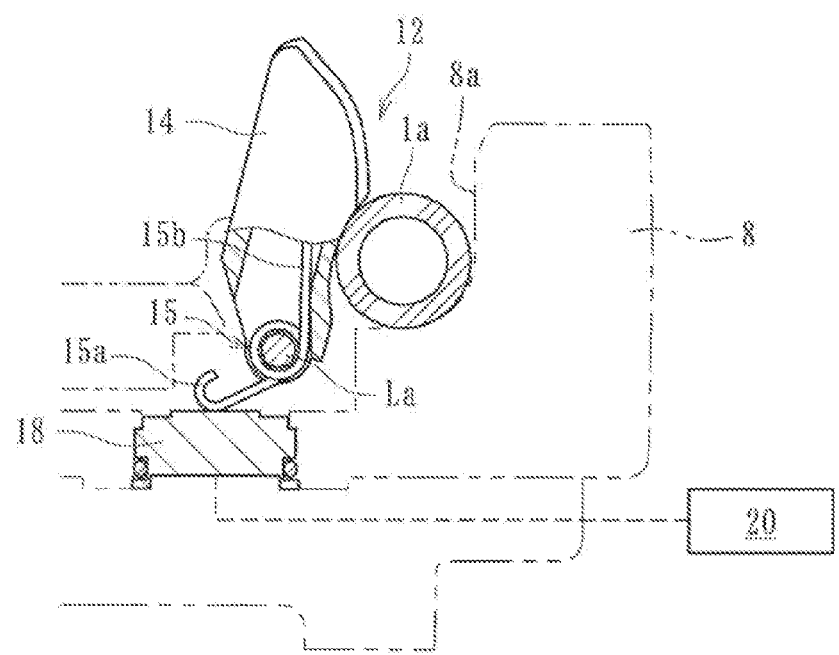

[Fig 5]
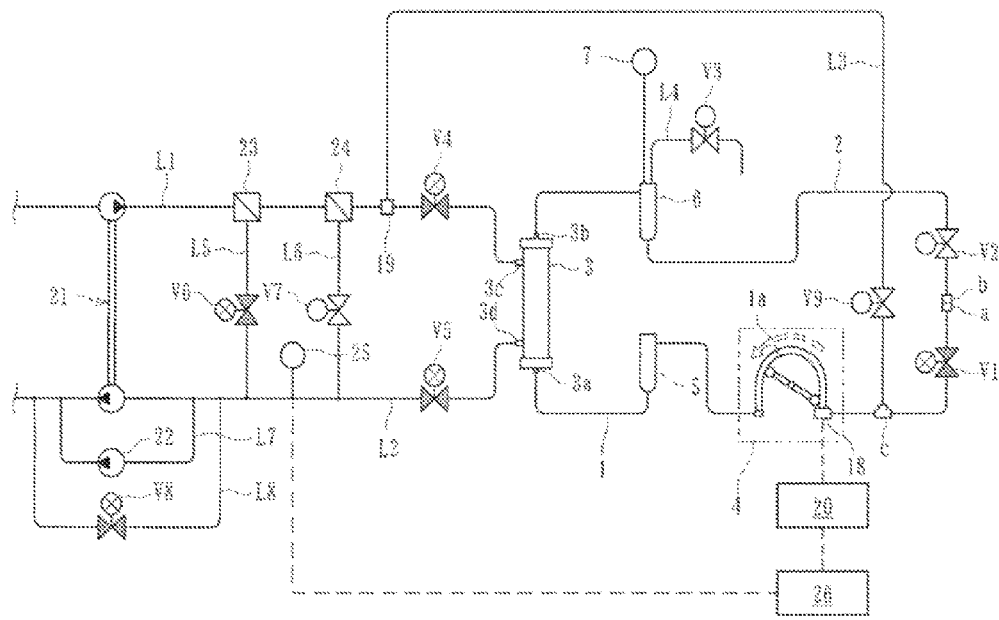

[Fig 6]
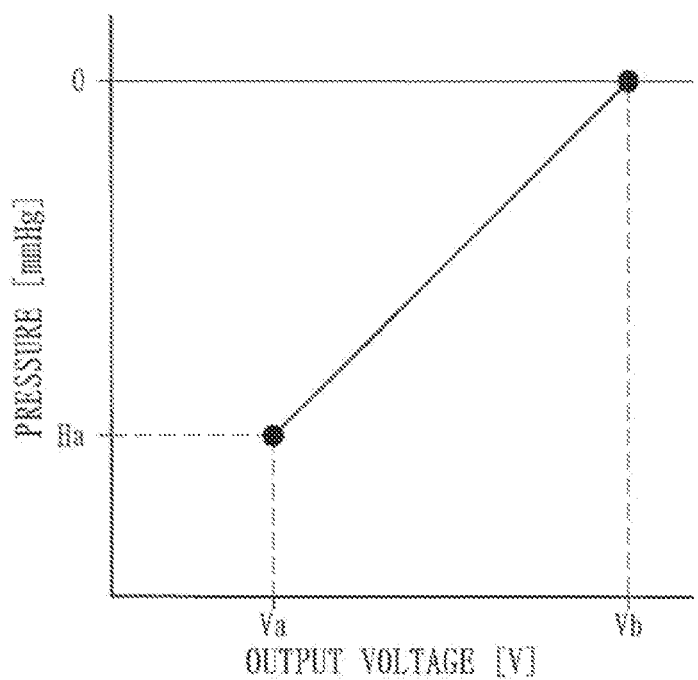
[Fig 7]
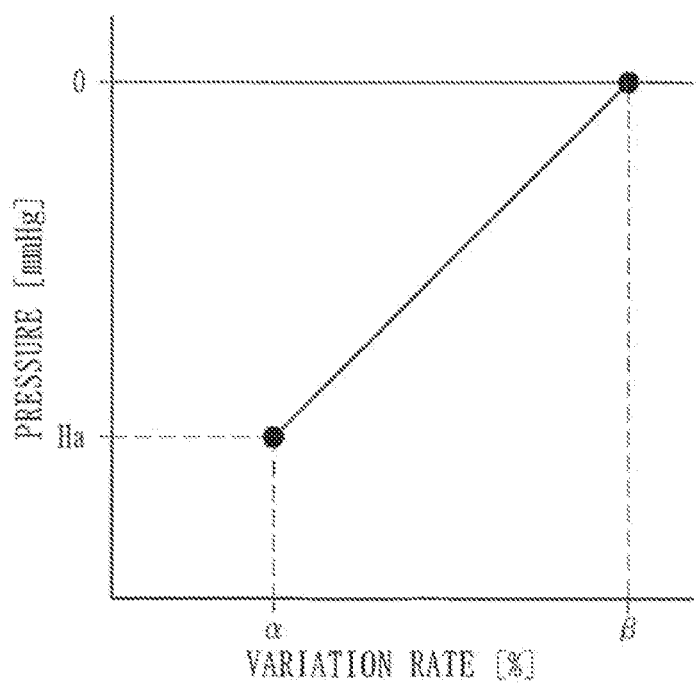

[Fig 8]
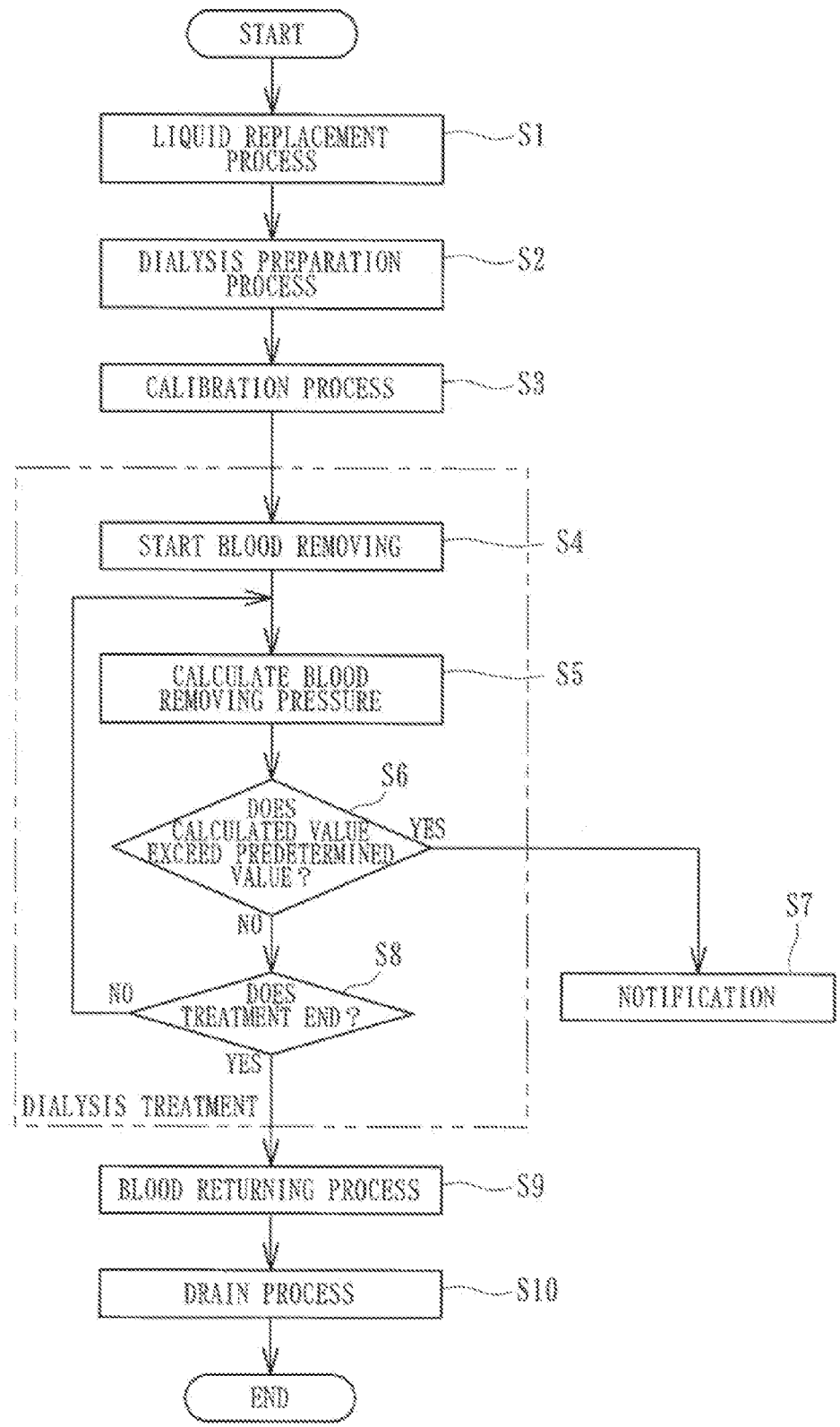

[Fig 9]
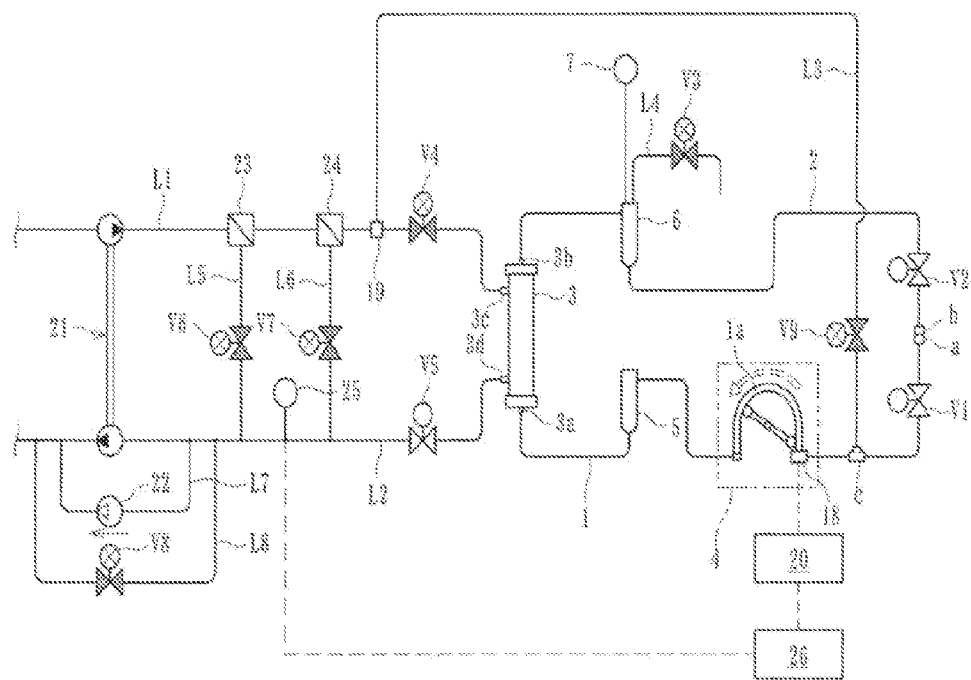

[Fig 10]
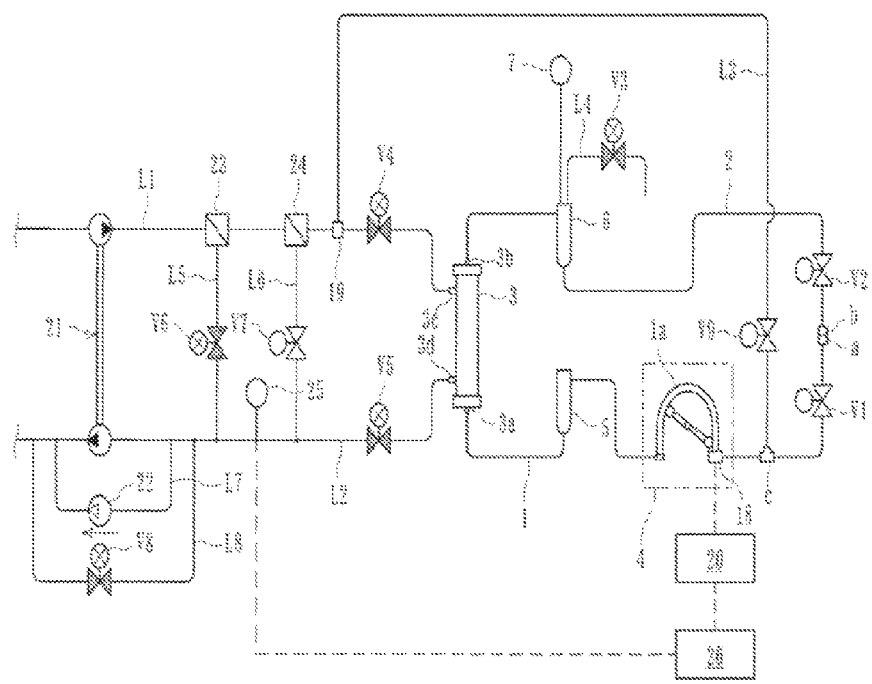

[Fig 11]
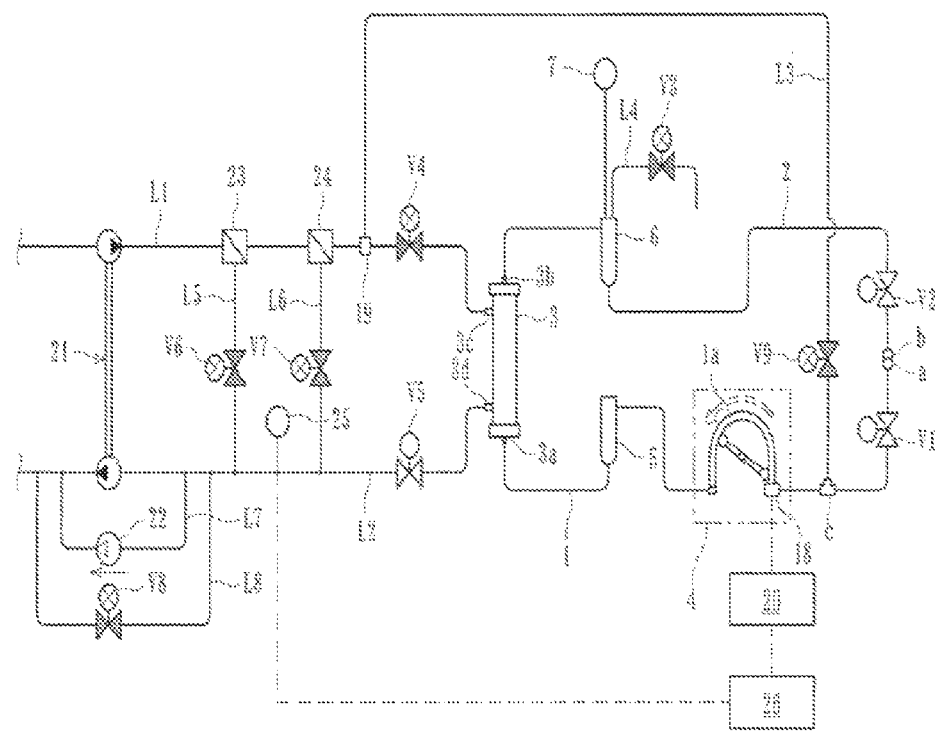

[Fig 12]
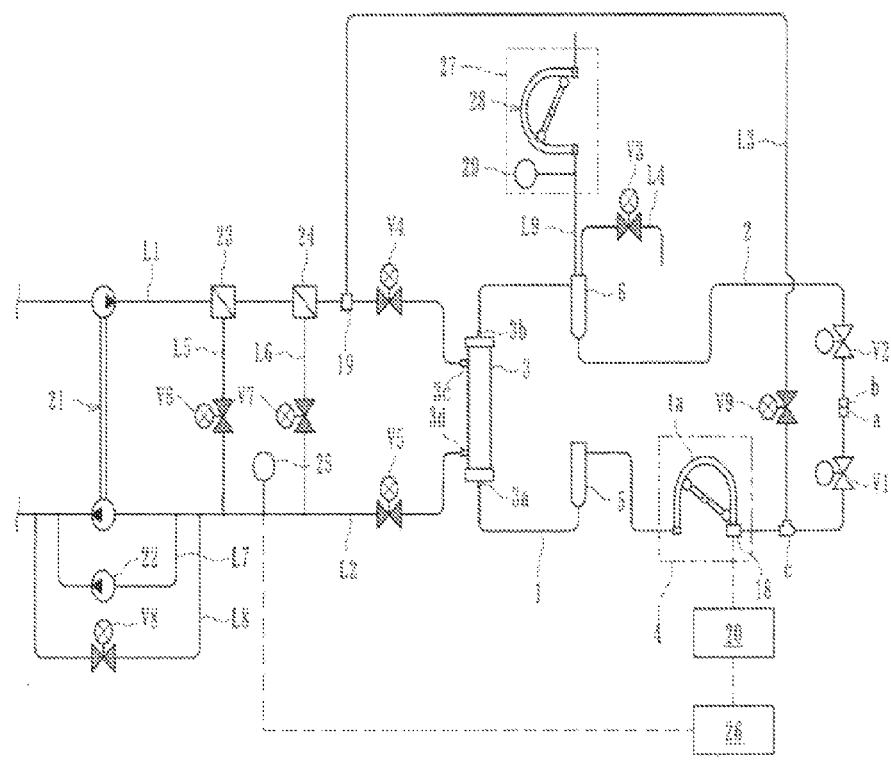

[Fig 13]
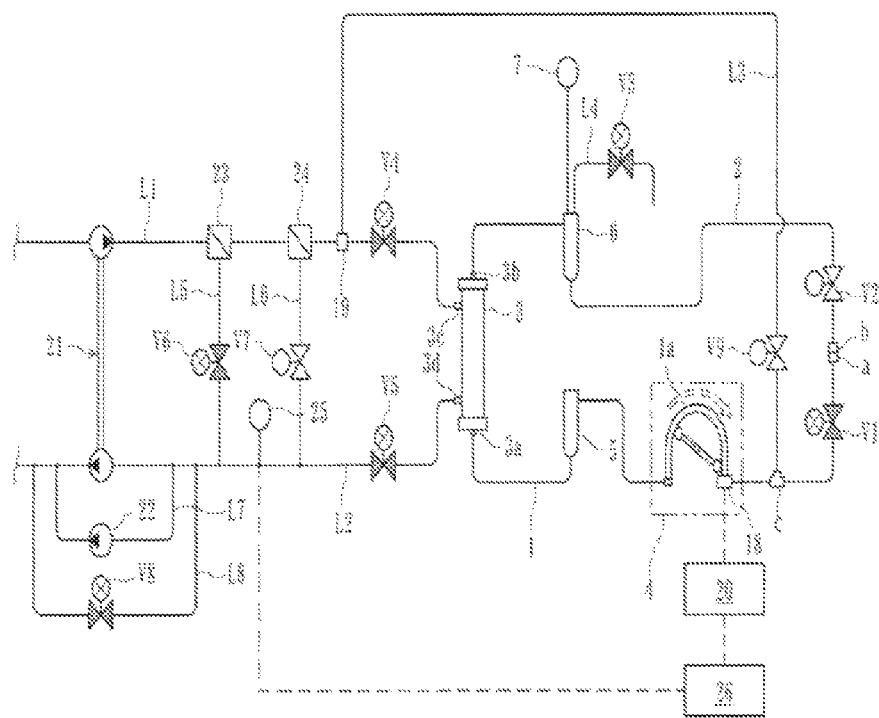

[Fig 14]
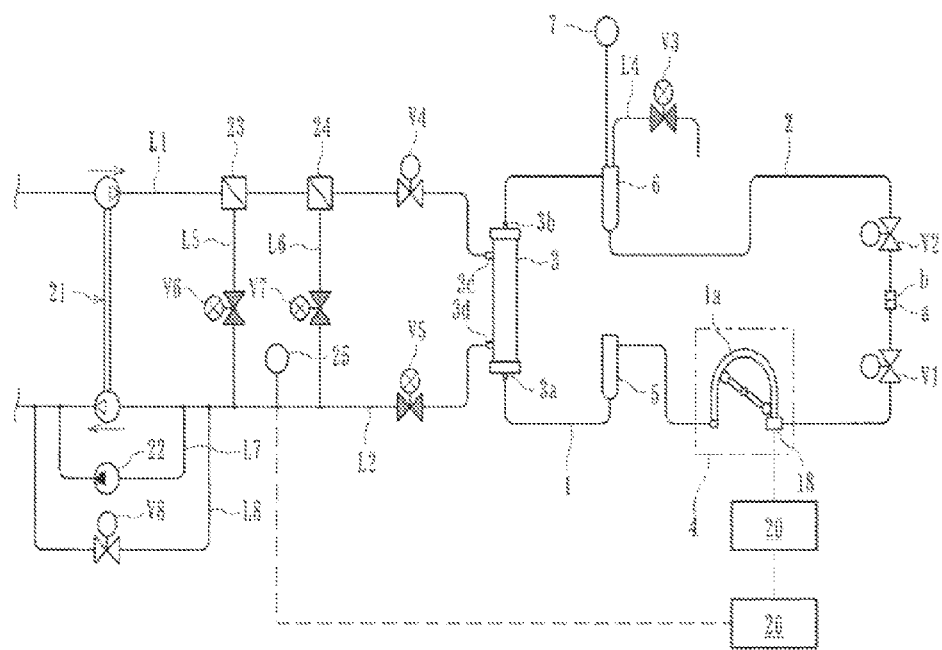

[Fig 15]
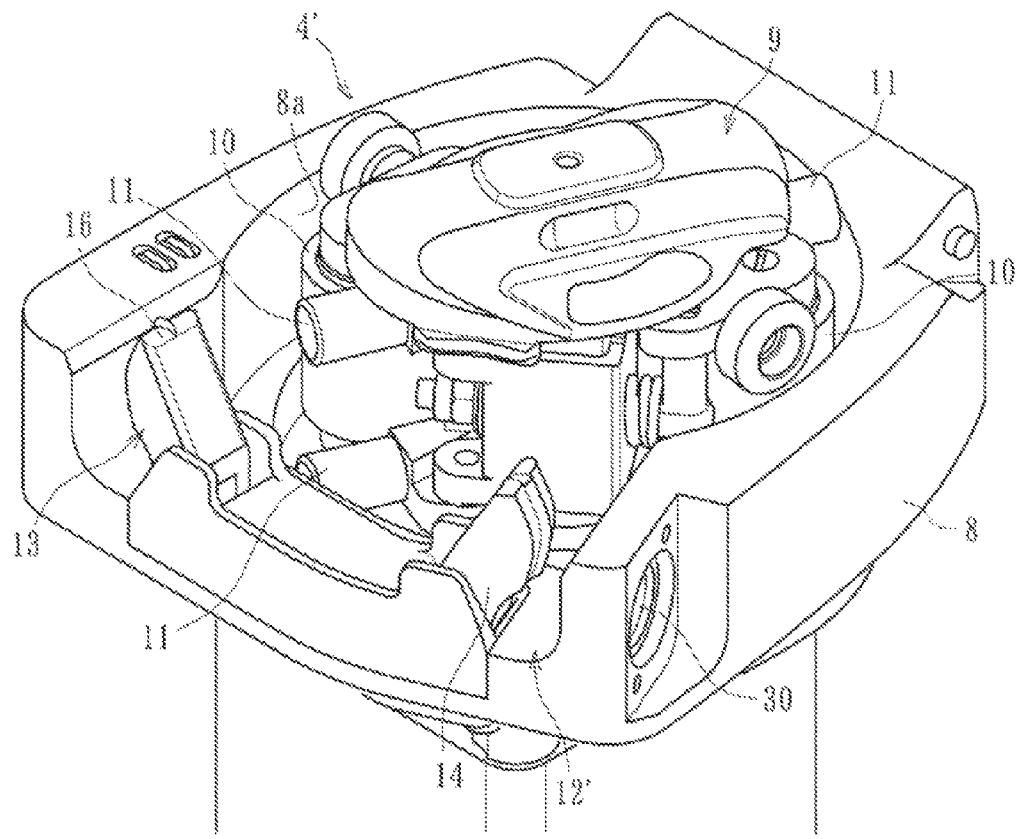
[Fig 16]
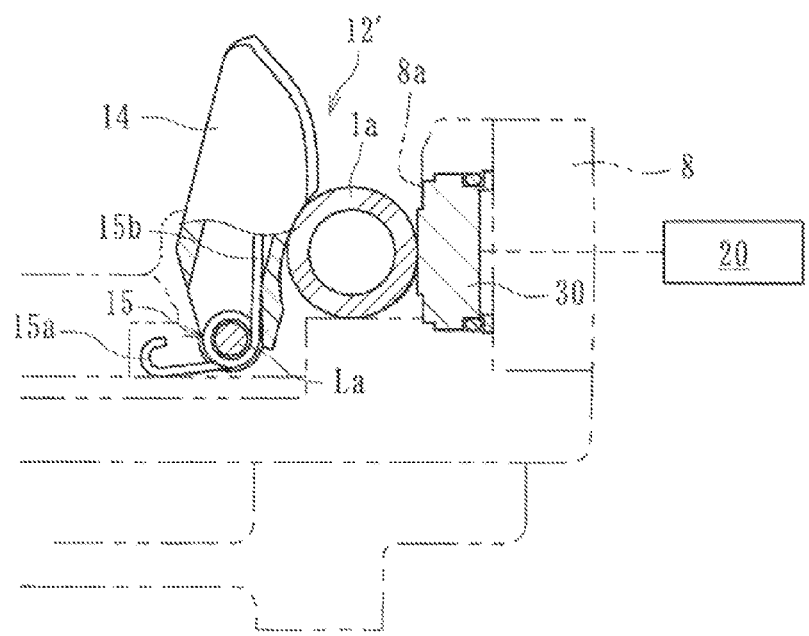

PRESSURE DETECTION DEVICE OF LIQUID FLOW ROUTE

FIELD

The present invention relates to a pressure detection device of a liquid flow route which detects pressure of the liquid flow route configured of a flexible tube, a portion of which is connected to a peristaltically-actuated tube that can cause an internal liquid to flow by being compressed in a radial direction and by being peristaltically actuated in a longitudinal direction by a peristalsis section of a peristaltic pump, and which enables a predetermined liquid to be circulated.

BACKGROUND

A general blood circuit used in hemodialysis treatment is mainly configured to include an arterial blood circuit in which an arterial puncture needle is attached to a distal end thereof and a venous blood circuit in which a venous puncture needle is attached to a distal end thereof. The blood circuit is configured so that a blood purifier such as a dialyzer can be connected to each base end of the arterial blood circuit and the venous blood circuit. A peristaltic blood pump is arranged in the arterial blood circuit and the blood pump is rotated in a state where both of the arterial puncture needle and the venous puncture needle puncture a patient. In this way, blood is collected through the arterial puncture needle and the blood is caused to flow in the arterial blood circuit and is introduced to the dialyzer. The blood purified by the dialyzer is configured to flow in the venous blood circuit and to return to the body of the patient internally via the venous puncture needle so as to perform dialysis treatment.

In addition, a negative pressure detection device (pressure detection device which usually detects a negative pressure is connected on an upstream side from the blood pump in the arterial blood circuit. The negative pressure detection device in the related art is configured of a member which is a so-called pillow configured to include a flexible hollow member having an internal space with a predetermined capacity if the blood flowing in the arterial blood circuit has a negative pressure, the negative pressure detection device is configured so as to be bent in a direction where a front surface portion and a rear surface portion become closer to each other (for example, refer to PTL 1). Then, for example, it is possible to detect the negative pressure by bringing a probe of the negative pressure detection device into contact with the front surface portion and the rear surface portion.

CITATION LIST

Patent Literature

PTL 1: Japanese Unexamined Patent Application Publication No. 2003-25601

SUMMARY

However, with regard to the pressure detection device in the related art, the flexible hollow member having the space with the predetermined capacity needs to be connected to the blood circuit (arterial blood circuit) in which the blood flows, thereby causing a problem in that the blood is likely to become sluggish inside the flexible hollow member. In addition, a separate flexible hollow member needs to be connected to the blood circuit, thereby causing a problem in that a manufacturing cost of the blood circuit is increased and the capacity of a liquid flow route in the blood circuit (priming volume) is increased.

The present applicants put forward using a peristaltically-actuated tube that can cause internal liquid (blood or the like) to flow by being compressed in a radial direction and by being peristaltically actuated in a longitudinal direction by a peristalsis section of a blood pump, and have studied a pressure detection device which can detect blood removal pressure of the arterial blood circuit (pressure between a distal end of the arterial blood circuit and the peristaltically-actuated tube) by detecting displacement of the peristaltically-actuated tube in the radial direction. Since the pressure detection device can detect the blood removal pressure using the peristaltically-actuated tube, it is possible to suppress the sluggishness of the circulated liquid and to decrease the manufacturing cost and capacity of the liquid flow route.

With regard to the pressure detection device, since there is a concern that an error due to a difference between separate devices such as the peristaltically-actuated tube or a sensor (displacement detecting means) for detecting the displacement of the peristaltically-actuated tube in the radial direction, it is predicted that it will be important to find some means and method in which calibration is performed so that the error is prevented. This problem is not limited to the pressure detection device of the blood circuit, but can arise in general pressure detection devices that can detect the pressure of a liquid flow route in which predetermined blood is circulated such that it is desirable to solve the problem.

The present invention is made in view of the above-described circumstances, and aims to provide a pressure detection device which can suppress sluggishness of a circulating liquid, decrease the manufacturing cost and the capacity of a liquid flow route, prevent an error due to a difference between separate peristaltically-actuated tubes or displacement detecting means, and detect the pressure in the liquid flow route with higher accuracy.

Solution to Problem

According to the invention described in the teachings herein, there is provided a pressure detection device of a liquid flow route which detects pressure of the liquid flow route configured of a flexible tube, a portion of which is connected to a peristaltically-actuated tube that can cause an internal liquid to flow by being compressed in a radial direction and by being peristaltically actuated in a longitudinal direction by a peristalsis section of a peristaltic pump, and which enables a predetermined liquid to be circulated, the pressure detection device including: displacement detecting means that detects displacement of the peristaltically-actuated tube in the radial direction; pressure calculating means that is able to calculate pressure of the liquid flow route based on the displacement of the peristaltically-actuated tube in the radial direction which is detected by the displacement detecting means; and calibration means that calibrates the displacement detecting means and the pressure calculating means. The calibration means includes closed flow route forming means that is able to form a closed flow route which includes a portion in the peristaltically-actuated tube at which the displacement detecting means is disposed, pressure changing means that is able to arbitrarily change the pressure in the flow route formed and closed by the closed flow route forming means, pressure detection means that is able to detect pressure change in the flow route formed and closed by the closed flow route forming means, and calibration curve acquiring means that is able to produce and acquire a calibration curve, with which the displacement detecting means and pressure calculating means are calibrated, by a relationship between the pressure change detected by the pressure detection means when the pressure is changed by the pressure changing means and a detection value of the displacement detecting means.

The invention according to the teachings herein provides the pressure detection device of a liquid flow route according to the teachings herein in which the peristaltically-actuated tube is connected to an intermediate portion of an arterial blood circuit that extracorporeally circulates blood of a patient at the time of a blood purification treatment, the peristaltic pump is a blood pump that causes the blood in the arterial blood circuit to flow, and blood removal pressure in the liquid flow route from a tip of the arterial blood circuit to the peristaltically-actuated tube is caused to be calculated by the displacement detecting means and the pressure calculating means in an extracorporeally circulating process of the blood at the time of the blood purification treatment and a blood returning process.

The invention according to the teachings herein provides the pressure detection device of a liquid flow route according to the teachings herein in which the pressure changing means is a pump which is rotated at the time of the blood purification treatment and the pressure detection means is a sensor which detects pressure at the time of the blood purification treatment.

The invention according to the teachings herein provides the pressure detection device of a liquid flow route according to the teachings herein in which the calibration of the displacement detecting means and the pressure calculating means is performed for each blood purification treatment by the calibration means.

The invention according to the teachings herein provides the pressure detection device of a liquid flow route according to the teachings herein in which the pressure changing means generates a negative pressure in the flow route formed and closed by the closed flow route forming means so as to change pressure in the flow route.

The invention according to the teachings herein provides the pressure detection device of a liquid flow route according to the teachings herein in which the pressure changing means generates a negative pressure and a positive pressure in the flow route formed and closed by the closed flow route forming means so as to change the pressure in the flow route.

The invention according to the teachings herein provides the pressure detection device of a liquid flow route according to the teachings herein in which the calibration curve acquiring means is able to produce and acquire a calibration curve with a pressure difference based on a difference between dispositional heights of the displacement detecting means and the pressure detection means taken into account.

The invention according to the teachings herein provides the pressure detection device of a liquid flow route according to the teachings herein which further includes: notifying means that is able to perform notification under a condition that the blood removal pressure calculated by the displacement detecting means and the pressure detection means exceeds a preset value.

The invention according to the teachings herein provides the pressure detection device of a liquid flow route according to the teachings herein in which the peristaltic pump includes grasping means that grasps the peristaltically-actuated tube mounted on the peristaltic pump and the displacement detecting means is able to detect displacement in the radial direction of a portion grasped by the grasping means.

The invention according to the teachings herein provides the pressure detection device of a liquid flow route according to the teachings herein in which the grasping means has a grasping piece that presses the peristaltically-actuated tube in the radial direction so as to grasp the peristaltically-actuated tube and biasing means that biases the grasping piece against the peristaltically-actuated tube and the displacement detecting means detects a load applied on a fixed end side of the biasing means and detects displacement of the peristaltically-actuated tube in the radial direction based on the detected load.

The invention according to the teachings herein provides the pressure detection device of a liquid flow route according to the teachings herein in which the grasping means has a grasping piece that presses the penstaltically-actuated tube in the radial direction so as to grasp the peristaltically-actuated tube and biasing means that biases the grasping piece against the peristaltically-actuated tube and the displacement detecting means is provided on a portion facing the grasping piece with the peristaltically-actuated tube interposed therebetween, detects pressure which is imparted on the side surface of the peristaltically-actuated tube pressed by the grasping piece, and detects displacement of the peristaltically-actuated tube in the radial direction based on the detected pressure.

According to the invention described in the teachings herein, there is provided a peristaltic pump that includes the pressure detection device of a liquid flow route according to the teachings herein.

According to the invention described in the teachings herein, there is provided a blood purification apparatus that includes the peristaltic pump according to the teachings herein.

Advantageous Effects of Invention

According to the teachings herein, since it is possible to detect pressure of the liquid flow route by the displacement detecting means that detects the displacement of the peristaltically-actuated tube in the radial direction, there is no need to connect separate means, which detects pressure, to the liquid flow route. Thus, it is possible to suppress sluggishness of a circulating liquid and to decrease a manufacturing cost and capacity of the liquid flow route.

Further, according to the teachings herein, the pressure detection device includes the calibration means that has the closed flaw route forming means, the pressure changing means, the pressure detection means, and the calibration curve acquiring means and the displacement detecting means and the pressure calculating means are calibrated by the calibration means. Therefore, it is possible to prevent an error based on a difference between separate peristaltically-actuated tubes or displacement detecting means and to detect the pressure in the liquid flow route with higher accuracy.

According to the teachings herein, since the blood removal pressure in the liquid flow route from the tip of the arterial blood circuit to the peristaltically-actuated tube is caused to be calculated by the displacement detecting means and the pressure calculating means in an extracorporeally circulating process of the blood at the time of the blood purification treatment and in a blood returning process, it is possible to monitor the blood removal pressure during the blood purification treatment or during the blood returning with higher accuracy.

According to the teachings herein, the pressure changing means is a pump which is rotated at the time of the blood purification treatment and the pressure detection means is a sensor which detects pressure at the time of the blood purification treatment. Therefore, it is possible to divert the pump and the sensor utilized at the time of the blood purification treatment as a configurational element of the calibration means.

According to the teachings herein, the calibration of the displacement detecting means and the pressure calculating means is performed for each blood purification treatment by the calibration means. Therefore, each time of the blood purification treatment, it is possible to prevent an error based on a difference between the separate peristaltically-actuated tubes or the displacement detecting means and to monitor the blood removal pressure during the blood purification treatment with higher accuracy.

According to the teachings herein, the pressure changing means generates a negative pressure in the flow route formed and closed by the closed flow route forming means so as to change pressure in the flow route. Therefore, it is possible to reproduce the same conditions as in a case where the negative pressure is generated at the time of blood removal in the blood purification treatment and to perform the calibration of the displacement detecting means and the pressure calculating means with higher accuracy.

According to the teachings herein, the pressure changing means generates a negative pressure and a positive pressure in the flow route formed and closed by the closed flow route forming means so as to change the pressure in the flow route. Therefore, it is possible to reproduce the same conditions as in a case where the negative pressure is generated at the time of blood removal in the blood purification treatment and a case where the blood pump is reversely rotated during the blood returning or the like and to perform the calibration of the displacement detecting means and the pressure calculating means with higher accuracy.

According to the teachings herein, the calibration curve acquiring means is able to produce and acquire a calibration curve with a pressure difference based on a difference between dispositional heights of the displacement detecting means and the pressure detection means taken into account. Therefore, it is possible to prevent an error based on the difference between dispositional heights of the displacement detecting means and the pressure detection means and to perform the calibration of the displacement detecting means with still higher accuracy.

According to the teachings herein, the pressure detection device further includes the notifying means that is able to perform notification under a condition that the blood removal pressure calculated by the displacement detecting means and the pressure detection means exceeds a preset value. Therefore, it is possible to promptly notify medical staff around of blood removal failure and to perform subsequent treatment more smoothly.

According to the teachings herein, the peristaltic pump includes grasping means that grasps the peristaltically-actuated tube mounted on the peristaltic pump and the displacement detecting means is able to detect displacement in the radial direction of a portion grasped by the grasping means. Therefore, the peristaltically-actuated tube is mounted on the peristaltic pump and, is grasped by the grasping means and, thereby, the peristaltically-actuated tube is mounted with respect to the pressure detection device. In this way, it is possible to lower a work burden on medical staff or the like.

According to the teachings herein, the grasping means has the grasping piece that presses the peristaltically-actuated tube in the radial direction so as to grasp the peristaltically-actuated tube and the biasing means that biases the grasping piece against the peristaltically-actuated tube and the displacement detecting means detects a load applied on a fixed end side of the biasing means and detects the displacement of the peristaltically-actuated tube in the radial direction based on the detected load. Therefore, it is possible for the peristaltic pump to fulfill both a function of enabling the biasing means to generate a grasping force with respect to the peristaltically-actuated tube and a function of detecting the pressure in the liquid flow route.

According to the teachings herein, the grasping means has the grasping piece that presses the peristaltically-actuated tube in the radial direction so as to grasp the peristaltically-actuated tube and the biasing means that biases the grasping piece against the peristaltically-actuated tube and the displacement detecting means is provided on the portion facing the grasping piece with the peristaltically-actuated tube interposed therebetween, detects the pressure which is imparted on the side surface of the peristaltically-actuated tube pressed by the grasping piece, and detects the displacement of the peristaltically-actuated tube in the radial direction based on the detected pressure. Therefore, it is possible for the displacement detecting means in the peristaltic pump to fulfill both a function of receiving a pressing force against the peristaltically-actuated tube and a function of detecting the pressure in the liquid flow route.

According to the teachings herein, it is possible to provide a peristaltic pump including the pressure detection device of a liquid flow route according to the teachings herein.

According to the teachings herein, it is possible to provide a blood purification apparatus including the peristaltic pump according to the teachings herein.

BRIEF DESCRIPTION OF DRAWINGS

FIG. 1 is a schematic view illustrating a blood circuit which employs a pressure detection device of a liquid flow route according to a first embodiment of the present invention.

FIG. 2 is a perspective view illustrating a blood pump in which the pressure detection device is arranged.

FIG. 3 is a plan view illustrating the blood pump in which the pressure detection device is arranged.

FIG. 4 is a schematic cross-sectional view illustrating displacement detecting means provided on the blood pump.

FIG. 5 is a schematic diagram illustrating a state of displacement detecting means in the pressure detection device at the time of calibration.

FIG. 6 is a graph illustrating a calibration curve with which the calibration of the displacement detecting means in the pressure detection device is performed.

FIG. 7 is a graph illustrating a calibration curve in another shape with which the calibration of the displacement detecting means in the pressure detection device is performed.

FIG. 8 is a flowchart illustrating the calibration of the displacement detecting means in the pressure detection device.

FIG. 9 is a schematic diagram illustrating a blood circuit (a state at the time of calibration) to which a pressure detection device of a liquid flow route according to a second embodiment of the present invention is applied.

FIG. 10 is a schematic diagram illustrating a blood circuit (a state at the time of calibration) to which a pressure detection device of a liquid flow route according to a third embodiment of the present invention is applied.

FIG. 11 is a schematic diagram illustrating a blood circuit (a state at the time of calibration) to which a pressure detection device of a liquid flow route according to a fourth embodiment of the present invention is applied.

FIG. 12 is a schematic diagram illustrating a blood circuit (a state at the time of calibration) to which a pressure detection device of a liquid flow route according to a fifth embodiment of the present invention is applied.

FIG. 13 is a schematic diagram illustrating a blood circuit (a state at the time of calibration with a positive pressure) to which a pressure detection device of a liquid flow route according to another embodiment of the present invention is applied.

FIG. 14 is a schematic diagram illustrating a blood circuit (a state at the time of calibration with a positive pressure) to which a pressure detection device of a liquid flow route according to still another embodiment of the present invention is applied.

FIG. 15 is a perspective view illustrating a blood pump in which a pressure detection device of a liquid flow route according to a sixth embodiment of the present invention is disposed.

FIG. 16 is a schematic cross-sectional view illustrating displacement detecting means provided on the blood pump.

DETAILED DESCRIPTION

Hereinafter, an embodiment of the present invention will be specifically described with reference to the drawings. The present application claims priority to Japanese Application No. 2012-231969, filed on Oct. 19, 2012 and International Application No. PCT/JP2013/078271, filed on Oct. 18, 2013 the teachings of which are incorporated by reference herein in their entirety for all purposes.

A pressure detection device according to a first embodiment detects pressure in a blood circuit (specifically, on the upstream side from a portion at which a blood pump is disposed) for performing a blood purification treatment (for example, a hemodialysis treatment) by extracorporeally circulating blood of a patient. As illustrated in FIG. 1, the blood circuit, to which the pressure detection device is applied, is mainly configured to have an arterial blood circuit 1, a venous blood circuit 2, and a dialyzer 3 as a blood purifier. The arterial blood circuit 1 corresponds to "a liquid flow route to which a peristaltically-actuated tube 1a is connected," of the present invention.

The arterial blood circuit 1 configures the liquid flow route configured of a flexible tube which can circulate a predetermined liquid. An arterial puncture needle (not illustrated) can be attached to a tip of the arterial blood circuit 1 via a connector a and an arterial air trap chamber 5 for removing bubbles is connected to an intermediate portion of the arterial blood circuit 1. One end of a dialysate supplying line L3 is connected to the arterial blood circuit 1 via a T shape tube c. The other end of the dialysate supplying line L3 is connected to a dialysate guiding-in line L1 via a collecting port 19. The dialysate supplying line L3 can be selectively opened and closed by an electromagnetic valve V9 and is configured to be able to supply dialysate of the dialysate guiding-in line L1 into the blood circuit.

In addition, the peristaltically-actuated tube 1a is connected to the intermediate portion (between the T shape tube c and the arterial air trap chamber 5) of the arterial blood circuit 1 and it is possible to mount the peristaltically-actuated tube 1a on the blood pump 4. The peristaltically-actuated tube 1a is compressed in the radial direction by rollers 10 (peristalsis section) of the blood pump 4 (peristaltic pump) and is peristaltically actuated in the longitudinal direction such that an internal liquid can flow in a rotating direction of a rotor 9 and is configured of a flexible tube which is more flexible and has a greater diameter than other flexible tubes which configure the arterial blood circuit 1. An electromagnetic valve V1 is disposed on the tip side of the arterial blood circuit 1 such that the flow route can be opened and closed at any timing.

The venous blood circuit 2 configures the liquid flow route that is formed of a flexible tube through which a predetermined liquid can circulate such that a venous puncture needle (not illustrated) can be attached to the tip thereof through a connector b and a venous air trap chamber 6 for removing bubbles is connected to an intermediate portion thereof. A flexible tube configuring the venous blood circuit 2 is substantially the same material and size of a diameter as the flexible tube configuring the arterial blood circuit 1. An electromagnetic valve V2 is disposed on the tip side of the venous blood circuit 2 such that the flow route can be opened and closed at any timing.

An overflow line L4 that can discharge air or gas in the venous air trap chamber 6 to the outside extends on an air layer side (upper section) of the venous air trap chamber 6 and an electromagnetic valve V3 that can open and close the flow route at any timing is disposed at an intermediate portion of the overflow line L4. Further, a pressure monitor line extending to the venous pressure sensor 7 extends on the air layer side (upper section) of the venous air trap chamber 6. The venous pressure sensor 7 measures pressure on the air layer side of the venous air trap chamber 6 and thereby, detects liquid pressure in the venous blood circuit 2 (venous pressure measured at the time of the blood purification treatment).

The dialyzer 3 is connected between the arterial blood circuit 1 and the venous blood circuit 2. After the arterial puncture needle and the venous puncture needle puncture the patient, the blood pump 4 is caused to normally rotate (an arrow direction of the blood pump 4 in FIG. 5) and thereby, the blood of the patient is caused to be extracorporeally circulated at the time of the blood purification treatment (dialysis treatment) through the liquid flow route that is configured of the arterial blood circuit 1, the venous blood circuit 2, and the dialyzer 3 (blood flow route).

On the other hand, before the blood purification treatment (before the dialysis treatment), as illustrated in FIG. 1, the connector a and the connector b are connected to each other and thereby, a tip of the arterial blood circuit 1 is connected to a tip of the venous blood circuit 2. Thus, this arterial blood circuit 1 and venous blood circuit 2 (including a blood flow route in the dialyzer 3) can form a closed circuit on the blood circuit side. The dialysate is supplied into the closed circuit through the dialysate supplying line L3 and thereby the blood circuit (the arterial blood circuit 1 and the venous blood circuit 2) is filled with the dialysate such that priming work can be performed. In a priming work process, the dialysate overflows from the overflow line L4 such that the inside of the closed circuit on the blood circuit is cleaned.

The dialyzer 3 is formed with multiple hollow fibers therein, in which minute holes (pores) are formed, in a casing section. A blood guiding-in port 3a, a blood guiding-out port 3b, a dialysate guiding-in port 3c, and a dialysate guiding-out port 3d are formed in the casing section, and base ends of the arterial blood circuit 1 and the venous blood circuit 2 are connected to the blood guiding-in port 3a and the blood guiding-out port 3b, respectively. In addition, the dialysate guiding-in port 3c and the dialysate guiding-out port 3d are connected, respectively, to a dialysate guiding-in line L1 and a dialysate discharging line L2 which extend from a dialysis apparatus main body.

The blood of the patient guided into the dialyzer 3 passes inside a hollow fiber membrane (blood flow route) in the dialyzer 3, and then is discharged from the blood guiding-out port 3b. The dialysate guided from the dialysate guiding-in port 3c passes outside a hollow fiber membrane (dialysate flow route), and then is discharged from the dialysate guiding-out port 3d. Accordingly, waste in the blood that passes through the blood flow route is caused to pass through to the dialysate side and can be purified, and it is possible for the purified blood to return into the body of the patient through the venous blood circuit 2.

The dialysis apparatus main body includes the dialysate guiding-in line L1 and the dialysate discharge line L2, and includes a duplex pump 21, bypass lines L5 to L8, and electromagnetic valves V4 to V8. Among them, the duplex pump 21 is disposed to straddle the dialysate guiding-in line L1 and the dialysate discharge line L2, and causes dialysate prepared to have a predetermined concentration to be guided into the dialyzer 3 and the dialysate to be discharged from the dialyzer 3.

The electromagnetic valve V4 is connected to an intermediate portion of the dialysate guiding-in line L1 (between the collecting port 19 and the dialyzer 3 on the dialysate guiding-in line L1) and the electromagnetic valve V5 is connected to an intermediate portion of the dialysate guiding-in line L2 (between a connection portion to the bypass line L6 on the dialysate discharge line L2 and the dialyzer 3). In addition, filters 23 and 24 are connected between the duplex pump 21 and the electromagnetic valve V4 on the dialysate guiding-in line L1.

The dialysate flowing through the dialysate guiding-in line L1 is subjected to filtration and is cleaned through filters 23 and 24 and the bypass lines L5 and L6 that guide the dialysate to bypass the dialysate discharge line L2 are connected to the filters 23 and 24, respectively. The bypass lines L5 and L6 are connected to the electromagnetic valves V6 and V7, respectively.

Liquid pressure measuring means 25 (dialysate pressure sensor) that can measure liquid pressure of the dialysate is disposed between a connection portion to the bypass line L5 and a connection portion to the bypass line L6 on the dialysate discharge line L2. The liquid pressure measuring means 25 can measure the pressure (liquid pressure) of the dialysate which is discharged from the dialyzer 3 and flows through the dialysate discharge line L2 at the time of the dialysis treatment (blood purification treatment).

Further, bypass lines L7 and L8 that bypass the duplex pump 21 are connected to the dialysate discharge line L2, respectively. An ultrafiltration pump 22 that removes water from the blood of the patient flowing in the blood flow route of the dialyzer 3 is disposed on the bypass line L7 and the electromagnetic valve V8 that can open and close the flow route is disposed on the bypass line L8. Although not illustrated in the drawings, a pump that adjusts the liquid pressure on the discharge side in the duplex pump 21 is disposed on the upstream side from the duplex pump 21 on the dialysate discharge line L2 (between a connection portion to the bypass line L7 and the duplex pump 21).

As illustrated in FIGS. 2 to 4, the blood pump 4 according to the present embodiment is mainly configured to include a stator 8, a rotor 9 which is rotatably driven inside the stator 8, rollers 10 (peristalsis section) formed in the rotor 9, a pair of upper and lower guide pins 11, upstream-side grasping means 12, downstream-side grasping means 13, and a load sensor 18 as displacement detection means. In the drawing, a cover that covers the upper section of the stator 8 in the blood pump 4 is omitted.

A mounting concave section 8a, on which the peristaltically-actuated tube 1a is mounted, is formed in the stator 8. The stator 8 is configured such that the peristaltically-actuated tube 1a is mounted along an inner circumferential wall surface which forms the mounting concave section 8a. The rotor 9 that is rotatable by a motor is provided substantially at the center of the mounting concave section 8a. A pair of rollers 10 and the guide pins 11 are provided on the side surface (surface facing the inner circumferential wall surface of the mounting concave section 8a) of the rotor 9.

The roller 10 is rotatable about a rotating shaft M formed on the outer edge side of the rotor 9 such that the roller 10 compresses the peristaltically-actuated tube 1a mounted on the mounting concave section 8a in the radial direction and causes the peristaltically-actuated tube 1a to be peristaltically actuated in the longitudinal direction (flowing direction of the blood) along with the rotation of the rotor 9 and, thereby, can cause the blood to flow in the arterial blood circuit 1. That is, when the peristaltically-actuated tube 1a is mounted on the mounting concave section 8a and the rotor 9 is rotated, the peristaltically-actuated tube 1a is compressed between the rollers 10 and the inner circumferential wall surface of the mounting concave section 8a and peristalsis can be performed in the rotating direction (longitudinal direction) along with the rotation of the rotor 9. Since the peristalsis causes the blood in the arterial blood circuit 1 to flow in the rotating direction of the rotor 9, it is possible to extracorporeally circulate the blood through the arterial blood circuit 1.

As illustrated in FIG. 2, the guide pins 11 are formed of a pair of upper and lower pin-shaped members which are formed to protrude toward the inner circumferential wall surface of the mounting concave section 8a from the upper end side and the lower end side of the rotor 9, respectively, and the peristaltically-actuated tube 1a is held between this pair of upper and lower guide pins 11. That is, the peristaltically-actuated tube 1a is held at a normal position by the pair of upper and lower guide pins 11 at the time of rotating of the rotor 9 and the peristaltically-actuated tube 1a is not separated upward from the mounting concave section 8a by the guide pin 11 on the upper side.

The upstream-side grasping means 12 is used for grasping the upstream side (a portion to which the tip side of the arterial blood circuit 1 is connected) of the penstaltically-actuated tube 1a that is mounted on the mounting concave section 8a of the stator 8 in the blood pump 4. As illustrated in FIGS. 2 to 4, the upstream-side grasping means 12 has a grasping piece 14 that presses the peristaltically-actuated tube 1a in the radial direction so as to grasp the peristaltically-actuated tube 1a and a torsion spring 15 (biasing means) which biases the grasping piece 14 against the peristaltically-actuated tube 1a.

As illustrated in FIG. 4, the grasping piece 14 is formed of components that are swing able about a swinging shaft 1a such that the grasping piece 14 is biased by the torsion spring 15 in a direction of grasping with a relatively strong force, presses a portion of the peristaltically-actuated tube 1a on the upstream side so as to fix and interpose the peristaltically-actuated tube 1a, and thereby, can be fixed. As illustrated in the same drawing, the torsion spring 15 is mounted on the swinging shaft La so as to bias the grasping piece 14 and has a fixed end 15a positioned at a fixed section of the stator 8 (according to the present embodiment, the load sensor 18 mounted on the stator 8) and a pressing end 15b that presses the grasping piece 14. Instead of the torsion spring 15, other biasing means that biases the grasping piece 14 may be used.

The downstream-side grasping means 13 is used for grasping the downstream side (a portion to which the base end side of the arterial blood circuit 1 is connected) of the peristaltically-actuated tube 1a that is mounted on the mounting concave section 8a of the stator 8 in the blood pump 4. The downstream-side grasping means 13 has a grasping piece 16 that presses the peristaltically-actuated tube 1*a* in the radial direction so as to grasp the peristaltically-actuated tube 1*a* and a torsion spring 17 which biases the grasping piece 16 against the peristaltically-actuated tube 1*a*.

The grasping piece 16 is formed of components that are swingable about a swinging shaft Lb such that similar to the grasping piece 14 of the upstream-side grasping means 12, the grasping piece 16 is biased by the torsion spring 17 in a direction of grasping with a relatively strong force, presses a portion of the peristaltically-actuated tube 1*a* on the downstream side so as to fix and interpose the peristaltically-actuated tube 1*a*, and thereby, can be fixed. Similar to the torsion spring 15 of the upstream-side grasping means 12, the torsion spring 17 is mounted on the swinging shaft Lb so as to bias the grasping piece 16 and has a fixed end positioned at a fixed section of the stator 8 and a pressing end that presses the grasping piece 16.

The load sensor 18 as the displacement detecting means can detect displacement in the radial direction of a portion of the peristaltically-actuated tube 1*a* which is grasped by the upstream-side grasping means 12. According to the present embodiment, a load applied on the fixed end 15*a* side of the torsion spring 15 (biasing means) is detected and the displacement of the peristaltically-actuated tube 1*a* in the radial direction is detected based on the detected load. The load sensor 18 can generate an electrical signal in accordance with the applied load.

That is, since the arterial puncture needle is attached to the tip of the arterial blood circuit at the time of the treatment, a negative pressure is generated between the tip of the arterial blood circuit 1 and the blood pump 4 when the blood which is collected from the patient flows in the arterial blood circuit 1 (flow in an arrow direction indicating the rotation direction of the blood pump 4 in FIG. 5). If a negative pressure is generated, liquid pressure inside the peristaltically-actuated tube 1*a* is decreased, and the portion grasped by the upstream-side grasping means 12 in the peristaltically-actuated tube 1*a* is displaced (diameter is decreased) in the radial direction. Thus, the load detected by the load sensor 18 is decreased. The decrease of the load is detected and thereby, it is possible to detect that a negative pressure is generated in the arterial blood circuit 1.

The load sensor 18 (displacement detecting means) according to the present embodiment is electrically connected to pressure calculating means 20 by extending a wire therein or the like. The pressure calculating means 20 is adapted to have, for example, a microcomputer or the like disposed in the dialysis apparatus main body or provided separately from the dialysis apparatus main body such that the pressure calculating means 20 is configured to calculate pressure in the arterial blood circuit 1 (liquid flow route) based on the displacement of the peristaltically-actuated tube 1*a* in the radial direction which is detected by the load sensor 18 (displacement detecting means). That is, when the displacement of the peristaltically-actuated tube 1*a* in the radial direction is detected by the load sensor 18, a predetermined electrical signal in accordance with the displacement is transmitted to the pressure calculating means 20 and the pressure (blood removal pressure at the time of the blood purification treatment) in the arterial blood circuit 1 (according to the present embodiment, portion from the tip of the arterial blood circuit 1 to a portion at which the load sensor 18 is disposed) is calculated by the pressure calculating means 20.

Here, according to the present embodiment, calibration means is provided, which performs calibration of the load sensor 18 (displacement detecting means) and the pressure calculating means 20. The calibration means is mainly configured to include closed flow route forming means (according to the present embodiment, electromagnetic valves V1 to V9), pressure changing means (according to the present embodiment, blood pump 4), pressure detection means (according to the present embodiment, the liquid pressure measuring means 25 (dialysate pressure sensor)), and calibration curve acquiring means 26.

The closed flow route forming means (according to the present embodiment, electromagnetic valves V1 to V9) can form a flow route that is closed (hereinafter, also referred to as a closed flow route) and includes a portion of the peristaltically-actuated tube 1*a* at which the load sensor 18 (displacement detecting means) is disposed. For example, the electromagnetic valves V1 to V9 are selectively electrified by control means that controls the present dialysis apparatus (blood purification apparatus) such that, as illustrated in FIG. 5, the electromagnetic valves V2, V3, V7, and V9 are in a state of being open and the other electromagnetic valves V1, V4 to V6, and V8 are in a state of being closed. In this state, the closed flow route including the portion at which the load sensor 18 is disposed (the flow routes on both the dialysis apparatus main body side and on the blood circuit side are targets) is formed.

The closed flow route formed by the closed flow route forming means is adapted to include the load sensor 18 and the liquid pressure measuring means 25 and pressure imparted to the load sensor 18 is set to be substantially the same as pressure detected by the liquid pressure measuring means 25. In the "flow route that is closed" (closed flow route) according to the present invention, when the pressure in the flow route is arbitrarily changed, the pressure (that is, pressure to be detected by the load sensor 18) imparted to the load sensor 18 (displacement detecting means) becomes substantially the same as the pressure detected by the liquid pressure measuring means 25.

The pressure changing means can arbitrarily change the pressure in the flow route formed and closed by the closed flow route forming means described above. The blood pump 4 which is a pump that is caused to rotate at the time of the dialysis treatment (at the time of the blood purification treatment) according to the present embodiment is diverted as the pressure changing means. That is, in addition to the load sensor 18 and the liquid pressure measuring means 25, the blood pump 4 is disposed in the closed flow route formed by the closed flow route forming means and it is possible to arbitrarily change the pressure in the closed flow route by causing the blood pump 4 to rotate.

According to the present embodiment, after the blood pump 4 as the pressure changing means is caused to normally rotate until the rotor 9 (peristalsis section) is half turned, the blood pump 4 stops and the pressure in the closed flow route is changed. In this way, according to the present embodiment, the blood pump 4 is caused to normally rotate and the flow route formed and closed by the closed flow route forming means has a negative pressure such that the pressure is changed.

Thus, the blood pump 4 as the pressure changing means causes the flow route formed and closed by the closed flow route forming means to have a negative pressure such that the pressure is changed. Therefore, it is possible to reproduce the same conditions as in a case where the negative pressure is generated at the time of blood removal in the blood purification treatment and to perform the calibration of the load sensor 18 and the pressure calculating means 20 with higher accuracy. According to the present embodiment, since the blood pump 4 during rotating functions as the pressure changing means and the blood pump 4 during stop of the rotation is in a state in which the peristaltically-actuated tube 1*a* is closed by the rollers 10, the blood pump 4 functions as one of the closed flow route forming means.

The pressure calculating means can detect a pressure change in the flow route formed and closed by the closed flow route forming means described above. According to the present embodiment, the liquid pressure measuring means 25 (dialysate pressure sensor) which detects pressure (dialysate pressure) at the time of the dialysis treatment (at the time of the blood purification treatment) is configured to be diverted as the pressure detection means. That is, since the blood pump 4 is caused to rotate such that the pressure in the closed flow route is changed, the pressure is detected by the liquid pressure measuring means 25 as the pressure detection means. In a configuration according to the present embodiment, the pressure (liquid pressure) before and after the blood pump 4 rotates (before the rotation and after the rotation) is detected by the liquid pressure measuring means 25.

The calibration curve acquiring means 26 can produce and acquire a calibration curve, with which the load sensor 18 and the pressure calculating means 20 are calibrated, from a relationship between the pressure change detected by the liquid pressure measuring means 25 (pressure detection means) when the pressure is changed (the pressure before and after the blood pump 4 is driven) by the blood pump 4 (pressure changing means) and the detection value (output voltage) of the load sensor 18 (displacement detecting means). For example, when the pressure detected by the liquid pressure measuring means 25 before the rotation of the blood pump 4 is 0, the detection value (output voltage) of the load sensor 18 is Vb. When the pressure detected by the liquid pressure measuring means 25 after the rotation of the blood pump 4 is Ha and the detection value (output voltage) of the bad sensor 18 is Va, a calibration curve (when pressure is y and an output voltage is x, y=ax−b) is obtained as illustrated in FIG. 6, based on a graph in which the vertical axis corresponds to the pressure (mmHg) and the horizontal axis corresponds to the output voltage (V) as in the drawing.

A method of obtaining the calibration curve is not limited thereto. For example, when the pressure detected by the liquid pressure measuring means 25 before the rotation of the blood pump 4 is 0 with a changing ratio (changing ratio with the ratio before the rotation of the blood pump 4 as 100%) of the detection values (output voltage) of the load sensor 18 (displacement detecting means) after the rotation of the blood pump 4 as a parameter, a changing ratio of the output voltages of the load sensor 18 is β (%) (100%). When the pressure detected by the liquid pressure measuring means 25 after the rotation of the blood pump 4 is Ha and the changing ratio of output voltage of the load sensor 18 is α (%), a calibration curve (when pressure is y and a changing ratio is x', y=ax'−b) is obtained as illustrated in FIG. 7, based on a graph in which the vertical axis corresponds to the pressure (mmHg) and the horizontal axis corresponds to the changing ratio (%) as in the drawing.

Based on the calibration curve obtained by the calibration curve acquiring means 26, the calibration of the load sensor 18 and the pressure calculating means 20 is performed and the calibrated load sensor 18 and pressure calculating means 20 detect blood removal pressure at the time of the dialysis treatment at the time of the blood purification treatment). That is, the calibrated load sensor 18 (displacement detecting means) and pressure calculating means 20 can calculate the blood removal pressure which is the pressure in the liquid flow route from the tip of the arterial blood circuit 1 to the peristaltically-actuated tube 1*a* in the extracorporeally circulating process of the blood at the time of the blood purification treatment.

According to the present embodiment, the calibration of the load sensor 18 (displacement detecting means) and the pressure calculating means 20 by the calibration means as described above is performed each time of the blood purification treatment (each time of the dialysis treatment) and the calibration of the load sensor 18 (displacement detecting means) and the pressure calculating means 20 in the calibration process before the blood purification treatment (dialysis treatment) is started is performed (refer to a flowchart in FIG. 8) in this way, each time of the blood purification treatment, it is possible to prevent an error based on a difference between separate devices of the peristaltically-actuated tube 1*a* and the load sensor 18 (displacement detecting means) and the blood removal pressure during the blood purification treatment is monitored with higher accuracy.

Further, it is preferable that the calibration curve acquiring means 26 produce and acquire a calibration curve with a pressure difference based on a difference between dispositional heights of the load sensor 18 (displacement detecting means) and the pressure detection means (according to the present embodiment, liquid pressure measuring means 25 (dialysate pressure sensor)) taken into account. That is, in a case where the dispositional height of the load sensor 18 is different from the dispositional height of the pressure detection means, the pressure difference is produced by the height difference. Since an error is produced by an equivalent amount, the calibration curve is produced and acquired with the pressure difference taken into account and then, it is possible to prevent the error based on the difference between dispositional heights of the load sensor 18 and the pressure detection means and to perform the calibration of the displacement detecting means with still higher accuracy.

Further, according to the present embodiment, notifying means is provided, which is able to perform notification under a condition that the blood removal pressure calculated by the load sensor 18 (displacement detecting means) and the pressure detection means 20 exceeds a preset value. The notifying means is adapted to have, for example, display means (touch panel or the like) disposed in the dialysis apparatus main body, a speaker, an external display lamp, or the like, and can perform notification (display on the display means, output of a warning through the speaker, turning-on or turning-off of the external display lamp, or the like) under a condition that the blood removal pressure exceeds the set value.

As above, when the notifying means which is able to perform notification under a condition that the blood removal pressure calculated by the load sensor 18 (displacement detecting means) and the pressure detection means 20 exceeds the preset value is provided, it is possible to promptly notify medical staff around of blood removal failure and to perform subsequent treatment more smoothly. Instead of or along with the notification of the notifying means, the dialysis treatment may be forcibly stopped under the condition that the blood removal pressure calculated by the load sensor 18 (displacement detecting means) and the pressure detection means 20 exceeds the preset value.

Next, control details of the dialysis apparatus (blood purification apparatus) according to the present embodiment will be described based on a flowchart in FIG. 8.

Before starting the dialysis treatment (blood purification treatment), first, a liquid replacement process S1 is performed, the inside of the tube in the dialysis apparatus main body is filled with the dialysate, and a self-examination such as a tube leakage examination or other test is performed. Then, the process proceeds to a dialysis preparation process S2, dialysis conditions are set, the peristaltically-actuated tube 1a is mounted on the blood pump 4 in the arterial blood circuit 1, and priming of the blood circuit or the substitution distributing (operation of filling with substitution solution) is performed. In parallel with the dialysis preparation process S2, the priming (gas purge) on the dialysate flow route side of the dialyzer 3 is also performed.

After the dialysis preparation process S2 ends, the process proceeds to a calibration process S3. In the calibration process S3, as described above, the closed flow route is formed by the closed flow route forming means, the blood pump 4 as the pressure changing means is caused to rotate, and the pressure (liquid pressure) in the closed flow route is arbitrarily changed. The pressure change is detected by the liquid pressure measuring means 25 as the pressure detection means, the calibration curve is produced and acquired by the calibration curve acquiring means 26 based on the detection and the calibration is performed.

The arterial puncture needle a and the venous puncture needle b puncture the patient, the blood pump 4 rotates, and thus the rollers 10 (peristalsis section) rotate such that the blood removing starts (start of blood removing S4). The blood of the patient extracorporeally circulates through the arterial blood circuit 1 and the venous blood circuit 2. Accordingly, the blood being subjected to the extracorporeally circulating process is purified in the dialyzer 3 and the dialysis treatment (blood purification treatment) is performed After the start of the blood removal, a blood removal pressure is calculated (S5) by the load sensor 18 (displacement detecting means) and the pressure calculating means 20 of which the calibration was performed in the calibration process (S3) and the blood removal pressure is monitored. Then, it is determined whether or not the blood removal pressure calculated in S5 exceeds a preset value (S6). In a case where the blood removal pressure exceeds the preset value, the process proceeds to S7 and predetermined notification is performed by the notifying means. In a case where the blood removal pressure does not exceed the preset value, the process proceeds to S8 and it is determined whether or not the dialysis treatment is ended. In S8, when it is determined that the dialysis treatment is not ended, the process returns to S5, and the blood removal pressure continues to be monitored.

On the other hand, when it is determined that the dialysis treatment is ended in S8, the process proceeds to S9, through a blood returning process S9 (process of returning blood in the blood circuit into the body of the patient), a discharge process S10 is performed, in which liquid purging of the dialyzer 3 is performed, and a series of control operations end. Through the series of processes described above, it is possible to detect the blood removal pressure during the dialysis treatment in real time and to monitor the blood removal state in the dialysis treatment (blood purification treatment).

According to the present embodiment, since the load sensor 18 (displacement detecting means), which detects the displacement of the peristaltically-actuated tube 1a in the radial direction, detects the pressure in the liquid flow route (blood removal pressure generated in the arterial blood circuit 1), there is no need to connect separate means which detects the pressure to the liquid flow route, and it is possible to suppress the sluggishness of the circulating liquid and to decrease the manufacturing cost and the capacity of the liquid flow route.

Further, according to the present embodiment, the calibration means includes the closed flow route forming means, the pressure changing means, the pressure detection means, and the calibration curve acquiring means 26 and the load sensor 18 (displacement detecting means) and the pressure calculating means 20 are calibrated by the calibration means. Therefore, it is possible to prevent an error based on a difference between separate peristaltically-actuated tubes 1a or the load sensor 18 (displacement detecting means) and to detect the pressure in the liquid flow route with higher accuracy.

In addition, according to the present embodiment, since the blood removal pressure in the liquid flow route from the tip of the arterial blood circuit 1 to the peristaltically-actuated tube 1a is caused to be calculated by the load sensor 18 (displacement detecting means) and the pressure calculating means 20 in an extracorporeally circulating process of the blood at the time of the blood purification treatment, it is possible to monitor the blood removal pressure during the blood purification treatment with higher accuracy. That is, the load sensor 18 (displacement detecting means) and the pressure calculating means 20 which are calibrated by the calibration means detect and monitor the blood removal pressure at the time of the blood purification treatment.

Further, according to the present embodiment, the pressure changing means is a blood pump 4 which is a pump and is rotated at the time of the blood purification treatment and the pressure detection means is the liquid pressure measuring means 25 (dialysate pressure sensor) as a sensor which detects pressure at the time of the blood purification treatment. Therefore, it is possible to divert the pump and the sensor utilized at the time of the blood purification treatment as a configurational element of the calibration means.

The blood pump 4 includes grasping means (upstream-side grasping means 12 and downstream-side grasping means 13) which grasps the peristaltically-actuated tube 1a mounted on the blood pump 4 and the load sensor 18 as the displacement detecting means is able to detect the displacement in the radial direction of a portion grasped by the upstream-side grasping means 12. Therefore, the peristaltically-actuated tube 1a is mounted on the blood pump 4 and is grasped by the upstream-side grasping means 12 and, thereby, the peristaltically-actuated tube 1a is mounted with respect to the pressure detection device. In this way, it is possible to lower a work burden on medical staff or the like.

Further, the upstream-side grasping means 12 includes the grasping piece 14 that presses the peristaltically-actuated tube 1a in the radial direction so as to grasp the peristaltically-actuated tube 1a and the torsion spring 15 (biasing means) that biases the grasping piece 14 to the peristaltically-actuated tube 1a side. The load sensor 18 as the displacement detecting means detects a load imparted on the fixed end 15a side of the torsion spring 15 and detects the displacement of the peristaltically-actuated tube 1a in the radial direction based on the detected load. Therefore, it is possible for the blood pump 4 to fulfill both a function of enabling the torsion spring 15 to generate a grasping force with respect to the peristaltically-actuated tube 1a and a function of detecting the pressure of the arterial blood circuit 1.

Further, the peristaltically-actuated tube 1a is connected to an intermediate portion of the arterial blood circuit 1 that extracorporeally circulates the blood of the patient at the time of the blood purification treatment (hemodialysis treatment), and the applied peristaltic pump is a blood pump 4 in the arterial blood circuit 1. Therefore, it is possible to monitor the negative pressure generated on the upstream side of the blood pump 4 in the arterial blood circuit 1. According to the present embodiment, it is possible to provide the peristaltic pump that includes the pressure detection device of the liquid flow route as described above and to provide the blood purification apparatus that includes the peristaltic pump.

Next, a second embodiment of the present invention will be described.

Similar to the first embodiment, the pressure detection device of the liquid flow route according to the present embodiment detects pressure in the blood circuit (specifically, on the upstream side from the portion on which the blood pump is disposed) which performs the blood purification treatment (for example, hemodialysis treatment) by the extracorporeal circulation of the blood of the patient. The applied blood circuit, the dialysis apparatus main body, the load sensor 18 (displacement detecting means), and the blood pump 4 that includes the load sensor 18 are configured to be the same as described in the first embodiment. The same reference signs are attached to the same components as those in the first embodiment and detailed description thereof is omitted.

Particularly, according to the present embodiment, the calibration means is provided, which is different from that in the first embodiment. As illustrated in FIG. 9, the calibration means according to the present embodiment is mainly configured to include the closed flow route forming means (according to the present embodiment, the electromagnetic valves V1 to V9), the pressure changing means (according to the present embodiment, the ultrafiltration pump 22), the pressure detection means (according to the present embodiment, the liquid pressure measuring means 25 (dialysate pressure sensor)), and the calibration curve acquiring means 26. The calibration according to the present embodiment is performed in a state in which the blood pump 4 and the duplex pump 21 are stopped.

The closed flow route forming means can form a flow route that is closed and includes a portion of the peristaltically-actuated tube 1a at which the load sensor 18 (displacement detecting means) is disposed. For example, the electromagnetic valves V1 to V9 are selectively electrified by the control means that controls the present dialysis apparatus (blood purification apparatus) such that, as illustrated in FIG. 9, the electromagnetic valves V1, V2, and V5 are in a state of being open and the other electromagnetic valves V3, V4, and V6 to V9 are in a state of being closed. In the state, the closed flow route including the portion at which the load sensor 16 is disposed (the flow routes on both the dialysis apparatus main body side and on the blood circuit side are targets) is formed. Since the blood pump 4 according to the present embodiment has a state of being stopped at the time of calibration, the blood pump 4 causes the peristaltically-actuated tube 1a to be closed by the rollers 10 and has a function of forming the closed flow route.

The pressure changing means can arbitrarily change the pressure in the flow route formed and closed by the closed flow route forming means described above. The ultrafiltration pump 22 which is a pump that is caused to rotate at the time of the dialysis treatment (at the time of the blood purification treatment) according to the present embodiment is configured to be diverted as the pressure changing means. That is, in addition to the load sensor 18 and the liquid pressure measuring means 25, the ultrafiltration pump 22 is disposed in the closed flow route formed by the closed flow route forming means and it is possible to arbitrarily change the pressure in the closed flow route by causing the ultrafiltration pump 22 to rotate.

According to the present embodiment, the ultrafiltration pump 22 as the pressure changing means is caused to rotate and the liquid (priming solution) in the blood circuits (arterial blood circuit 1 and venous blood circuit 2) is subjected to filtration from the blood flow route side to the dialysate flow route of the dialyzer 3, then, is discharged to the dialysate discharge line L2, and is discharged from the bypass line L7 through the dialysate discharge line L2. The pressure in the closed flow route is changed by an amount equal to the discharged dialysate.

The pressure detection means can detect a pressure change in the flow route formed and closed by the closed flow route forming means described above. Similar to the first embodiment, the liquid pressure measuring means 25 (dialysate pressure sensor) which detects pressure dialysate pressure) at the time of the dialysis treatment (at the time of the blood purification treatment) is configured to be diverted as the pressure detection means. The calibration curve acquiring means 26 can produce and acquire a calibration curve, with which the load sensor 18 and the pressure calculating means 20 are calibrated, by a relationship between the pressure change (pressure difference before and after the rotation of the ultrafiltration pump 22) detected by the liquid pressure measuring means 25 (pressure detection means) when the pressure is changed by the ultrafiltration pump 22 (pressure changing means) and the detection value (output voltage) of the load sensor 18 (displacement detecting means).

Based on the calibration curve obtained by the calibration curve acquiring means 26, the calibration of the load sensor 18 and the pressure calculating means 20 is performed and the calibrated load sensor 18 and pressure calculating means 20 detect blood removal pressure at the time of the dialysis treatment (at the time of the blood purification treatment). That is, the calibrated load sensor 18 (displacement detecting means) and pressure calculating means 20 can calculate the blood removal pressure which is the pressure in the liquid flow route from the tip of the arterial blood circuit 1 to the peristaltically-actuated tube 1a in the extracorporeally circulating process of the blood at the time of the blood purification treatment.

According to the present embodiment, the pressure changing means is the ultrafiltration pump 22 as a pump which is caused to rotate at the time of the blood purification treatment and the pressure detection means is the liquid pressure measuring means 25 (dialysate pressure sensor) as a sensor which detects the pressure at the time of the blood purification treatment. Therefore, in addition to the effects of the first embodiment, it is possible to divert the pump and the sensor utilized at the time of the blood purification treatment as components of the calibration means. As described in the first embodiment, the pressure changing means or the pressure detection means may use new means separate from the means utilized at the time of the blood purification treatment.

Next, a third embodiment of the present invention will be described.

Similar to the first embodiment, the pressure detection device of the liquid flow route according to the present embodiment detects pressure in the blood circuit (specifically, on the upstream side from the portion on which the blood pump is disposed) which performs the blood purification treatment (for example, hemodialysis treatment) by the extracorporeal circulation of the blood of the patient. The applied blood circuit, the dialysis apparatus main body, the load sensor 18 (displacement detecting means), and the blood pump 4 that includes the load sensor 18 are configured to be the same as described in the first embodiment. The same reference signs are attached to the same components as those in the first embodiment and detailed description thereof is omitted.

Particularly, according to the present embodiment, the calibration means is provided, which is different from that in the above embodiment. As illustrated in FIG. 10, the calibration means according to the present embodiment is mainly configured to include the closed flow route forming means (according to the present embodiment, the electromagnetic valves V1 to V9), the pressure changing means (according to the present embodiment, the ultrafiltration pump 22), the pressure detection means (according to the present embodiment, the liquid pressure measuring means 25 (dialysate pressure sensor)), and the calibration curve acquiring means 26. The calibration according to the present embodiment is performed in a state in which the blood pump 4 and the duplex pump 21 are stopped.

The closed flow route forming means can form a flow route that is closed and includes a portion of the peristaltically-actuated tube 1a at which the load sensor 18 (displacement detecting means) is disposed. For example, the electromagnetic valves V1 to V9 are selectively electrified by the control means that controls the present dialysis apparatus (blood purification apparatus) such that, as illustrated in FIG. 10, the electromagnetic valves V1, V2, V7, and V9 are in a state of being open and the other electromagnetic valves V3, V4 to V6, and V8 are in a state of being closed, in the state, the closed flow route including the portion at which the load sensor 18 is disposed (the flow routes on both the dialysis apparatus main body side and on the blood circuit side are targets) is formed. Since the blood pump 4 according to the present embodiment has a state of being stopped at the time of calibration, the blood pump 4 causes the peristaltically-actuated tube 1a to be closed by the rollers 10 and has a function of forming the closed flow route.

The pressure changing means can arbitrarily change the pressure in the flow route formed and closed by the closed flow route forming means described above. In the configuration, the ultrafiltration pump 22 which is a pump that is caused to rotate at the time of the dialysis treatment (at the time of the blood purification treatment) according to the present embodiment is diverted as the pressure changing means. That is, in addition to the load sensor 18 and the liquid pressure measuring means 25, the ultrafiltration pump 22 is disposed in the closed flow route formed by the closed flow route forming means and it is possible to arbitrarily change the pressure in the closed flow route by causing the ultrafiltration pump 22 to rotate.

According to the present embodiment, the ultrafiltration pump 22 as the pressure changing means is caused to rotate and the liquid (priming solution) in the blood circuits (artenal blood circuit 1 and venous blood circuit 2) flows to the dialysate guiding-in line L1 through the dialysate supplying line L3, reaches the dialysate discharge line L2 through bypass line L6, and is discharged from the bypass line L7 through the dialysate discharge line L2. The pressure in the closed flow route is changed by an amount equal to the discharged dialysate.

The pressure detection means can detect a pressure change in the flow route formed and closed by the closed flow route forming means described above. Similar to the first and second embodiments, in the configuration, the liquid pressure measuring means 25 (dialysate pressure sensor) which detects the pressure (dialysate pressure) at the time of the dialysis treatment (at the time of the blood purification treatment) is diverted as the pressure detection means. The calibration curve acquiring means 26 can produce and acquire the calibration curve, with which the load sensor 18 and the pressure calculating means 20 are calibrated, by a relationship between the pressure change (pressure difference before and after the rotation of the ultrafiltration pump 22) detected by the liquid pressure measuring means 25 (pressure detection means) when the pressure is changed by the ultrafiltration pump 22 (pressure changing means) and the detection value (output voltage) of the load sensor 18 (displacement detecting means).

Based on the calibration curve obtained by the calibration curve acquiring means 26, the calibration of the load sensor 18 and the pressure calculating means 20 is performed and the calibrated load sensor 18 and pressure calculating means 20 detect the blood removal pressure at the time of the dialysis treatment at the time of the blood purification treatment). That is, the calibrated load sensor 18 (displacement detecting means) and pressure calculating means 20 can calculate the blood removal pressure which is the pressure in the liquid flow route from the tip of the arterial blood circuit 1 to the peristaltically-actuated tube 1a in the extracorporeally circulating process of the blood at the time of the blood purification treatment.

According to the present embodiment, the pressure changing means is the ultrafiltration pump 22 as a pump which is caused to rotate at the time of the blood purification treatment and the pressure detection means is the liquid pressure measuring means 25 (dialysate pressure sensor) as a sensor which detects the pressure at the time of the blood purification treatment. Therefore, in addition to the effects of the first embodiment, it is possible to divert the pump and the sensor utilized at the time of the blood purification treatment as components of the calibration means. As described in the above embodiments, the pressure changing means or the pressure detection means may use new means separate from the means utilized at the time of the blood purification treatment.

Next, a fourth embodiment of the present invention will be described.

Similar to the first embodiment, the pressure detection device of the liquid flow route according to the present embodiment detects pressure in the blood circuit (specifically, on the upstream side from the portion on which the blood pump is disposed) which performs the blood purification treatment (for example, hemodialysis treatment) by the extracorporeal circulation of the blood of the patient. The applied blood circuit, the dialysis apparatus main body, the load sensor 18 (displacement detecting means), and the blood pump 4 that includes the load sensor 18 are configured to be the same as described in the above embodiments. The same reference signs are attached to the same components as those in the above embodiments and detailed description thereof is omitted.

Particularly, according to the present embodiment, the calibration means is provided, which is different from those in the above embodiments. As illustrated in FIG. 11, the calibration means according to the present embodiment is mainly configured to include the closed flow route forming means (according to the present embodiment, the electromagnetic valves V1 to V9), the pressure changing means (according to the present embodiment, the blood pump 4 and the ultrafiltration pump 22), the pressure detection means (according to the present embodiment, the liquid pressure measuring means 25 (dialysate pressure sensor)), and the calibration curve acquiring means 26. The calibration according to the present embodiment is performed in a state in which the duplex pump 21 is stopped.

The closed flow route forming means can form a flow route that is closed and includes a portion of the peristaltically-actuated tube 1*a* at which the load sensor 18 (displacement detecting means) is disposed. For example, the electromagnetic valves V1 to V9 are selectively electrified by the control means that controls the present dialysis apparatus (blood purification apparatus) such that, as illustrated in FIG. 11, the electromagnetic valves V1, V2, and V5 are in a state of being open and the other electromagnetic valves V3, V4, and V6 to V9 are in a state of being closed. In the state, the closed flow route including the portion at which the load sensor 18 is disposed (the flow routes on both the dialysis apparatus main body side and on the blood circuit side are targets) is formed.

The pressure changing means can arbitrarily change the pressure in the flow route formed and closed by the closed flow route forming means described above. In the configuration, the blood pump 4 and the ultrafiltration pump 22 which are pumps that are caused to rotate at the time of the dialysis treatment (at the time of the blood purification treatment) according to the present embodiment are diverted as the pressure changing means. That is, in addition to the load sensor 18 and the liquid pressure measuring means 25, the blood pump 4 and the ultrafiltration pump 22 are disposed in the closed flow route formed by the closed flow route forming means and it is possible to arbitrarily change the pressure in the closed flow route by causing the blood pump 4 and the ultrafiltration pump 22 to rotate.

According to the present embodiment, the blood pump 4 as the pressure changing means and the ultrafiltration pump 22 are caused to rotate. The liquid (priming solution) in the blood circuits (arterial blood circuit 1 and venous blood circuit 2) flows in the blood circuit and a part of the liquid is subjected to filtration from the blood flow route side to the dialysate flow route side of the dialyzer 3 and is discharged from the bypass line L7 through the dialysate discharge line L2. Therefore, the pressure in the closed flow route is changed by an amount equal to the discharged dialysate.

The pressure detection means can detect the pressure change in the flow route formed and closed by the closed flow route forming means described above. Similar to the first to third embodiments, in the configuration, the liquid pressure measuring means 25 (dialysate pressure sensor) which detects the pressure (dialysate pressure) at the time of the dialysis treatment (at the time of the blood purification treatment) is diverted as the pressure detection means. In addition, the calibration curve acquiring means 26 can produce and acquire the calibration curve, with which the load sensor 18 and the pressure calculating means 20 are calibrated, by a relationship between the pressure change (pressure difference before and after the rotation of the blood pump 4 and the ultrafiltration pump 22) detected by the liquid pressure measuring means 25 (pressure detection means) when the pressure is changed by the blood pump 4 and the ultrafiltration pump 22 (pressure changing means) and the detection value (output voltage) of the load sensor 18 (displacement detecting means).

Based on the calibration curve obtained by the calibration curve acquiring means 26, the calibration of the load sensor 18 and the pressure calculating means 20 is performed and the calibrated load sensor 18 and pressure calculating means 20 detect the blood removal pressure at the time of the dialysis treatment (at the time of the blood purification treatment). That is, the calibrated load sensor 18 (displacement detecting means) and pressure calculating means 20 can calculate the blood removal pressure which is the pressure in the liquid flow route from the tip of the arterial blood circuit 1 to the peristaltically-actuated tube 1*a* in the extracorporeally circulating process of the blood at the time of the blood purification treatment.

According to the present embodiment, the pressure changing means is adapted to have the blood pump 4 and the ultrafiltration pump 22 as pumps which are caused to rotate at the time of the blood purification treatment and the pressure detection means is the liquid pressure measuring means 25 (dialysate pressure sensor) as a sensor which detects the pressure at the time of the blood purification treatment. Therefore, in addition to the effects of the first embodiment, it is possible to divert the pump and the sensor utilized at the time of the blood purification treatment as components of the calibration means. As described in the above embodiments, the pressure changing means or the pressure detection means may use new means separate from the means utilized at the time of the blood purification treatment.

Next, a fifth embodiment of the present invention will be described.

Similar to the first embodiment, the pressure detection device of the liquid flow route according to the present embodiment detects pressure in the blood circuit (specifically, on the upstream side from the portion on which the blood pump is disposed) which performs the blood purification treatment (for example, hemodialysis treatment) by the extracorporeal circulation of the blood of the patient. The applied blood circuit (here, except for a liquid level adjusting means 27 illustrated in FIG. 12), the dialysis apparatus main body, the load sensor 18 (displacement detecting means), and the blood pump 4 that includes the load sensor 18 are configured to be the same as described in the above embodiments. The same reference signs are attached to the same components as those in the above embodiments and detailed description thereof is omitted.

The liquid level adjusting means 27 that adjusts a liquid level in the venous air trap chamber 6 before and during the blood purification treatment is disposed in the venous air trap chamber 6 of the venous blood circuit 2, as illustrated in FIG. 12. As illustrated in the drawing, the liquid level adjusting means 27 is connected to a pressure monitor line L9 extending from the air layer side (upper section) of the venous air trap chamber 6 and is configured to have a venous pressure sensor 29 and a peristaltic pump 28. The pressure monitor line L9 diverges at an intermediate portion and has a portion which is connected to the venous pressure sensor 29 and a portion at which the peristaltic pump 28 is disposed and the tips are opened.

The venous pressure sensor 29 is connected to the pressure monitor line L9 as described above and is configured to measure pressure on the air layer side of the venous air trap chamber 6 and to detect a liquid pressure (venous pressure measured at the time of the blood purification treatment) in the venous blood circuit 2. The peristaltic pump 28 can perform normal rotation and reverse rotation. The peristaltic pump 28 is configured to release the air in the venous air trap chamber 6 to the outside and the liquid level is raised by the normal rotation and to guide the air into the venous air trap chamber 6 and the liquid level is lowered by the reverse rotation.

According to the present embodiment, the calibration means includes the liquid level adjusting means 27 described above. As illustrated in FIG. 12, the calibration means according to the present embodiment is mainly configured to include the closed flow route forming means (according to the present embodiment, the electromagnetic valves V1 to V9), the pressure changing means (according to the present embodiment, the peristaltic pump 28 of the liquid level adjusting means 27), the pressure detection means (according to the present embodiment, the liquid pressure sensor 29), and the calibration curve acquiring means 26. The calibration according to the present embodiment is performed in a state in which the blood pump 4, the duplex pump 21, and the ultrafiltration pump 22 are stopped; however, the duplex pump 21 and the ultrafiltration pump 22 may rotate.

The closed flow route forming means can form a flow route that is closed and includes a portion of the peristaltically-actuated tube 1a at which the load sensor 18 (displacement detecting means) is disposed. For example, the electromagnetic valves V1 to V9 are selectively electrified by the control means that controls the present dialysis apparatus (blood purification apparatus) such that, as illustrated in FIG. 12, the electromagnetic valves V1 and V2 are in a state of being open and the other electromagnetic valves V3 to V9 are in a state of being closed. In the state, the closed flow route including the portion at which the load sensor 18 is disposed (the flow routes on both the dialysis apparatus main body side and on the blood circuit side are targets) is formed. Since the blood pump 4 according to the present embodiment is in the state of be stopped at the time of the calibration, the blood pump 4 has a function of closing the peristaltically-actuated tube 1a by the rollers 10 and forming the closed flow route. In addition, in a case where the duplex pump 21 and the ultrafiltration pump 22 rotate, the electromagnetic valves V1, V2, and V6 to V9 are in a state of being open and the electromagnetic valves V3 to V5 are in a state of being closed.

The pressure changing means can arbitrarily change the pressure in the flow route formed and closed by the closed flow route forming means described above. In the configuration, the peristaltic pump 28 of the liquid level adjusting means 27 which is a pump that is caused to rotate at the time of the dialysis treatment (at the time of the blood purification treatment) according to the present embodiment is diverted as the pressure changing means. That is, in addition to the load sensor 18 and the venous pressure sensor 29, the peristaltic pump 28 of the liquid level adjusting means 27 is disposed in the closed flow route formed by the closed flow route forming means and it is possible to arbitrarily change the pressure in the closed flow route by causing the peristaltic pump 28 to rotate.

According to the present embodiment, the peristaltic pump 28 as the pressure changing means is caused to normally rotate. The liquid (priming solution) in the blood circuits (arterial blood circuit 1 and venous blood circuit 2) flows toward the air layer of the venous air trap chamber 6 and the pressure in the closed flow route is changed by an amount equal to the flowing liquid.

The pressure detection means can detect the pressure change in the flow route formed and closed by the closed flow route forming means described above. According to the present embodiment, in the configuration, the venous pressure sensor 29 which detects the venous pressure during the blood purification treatment is diverted as the pressure detection means. In addition, the calibration curve acquiring means 26 can produce and acquire the calibration curve, with which the load sensor 18 and the pressure calculating means 20 are calibrated, by a relationship between the pressure change (pressure difference before and after the rotation of the peristaltic pump 28) detected by the venous pressure sensor 29 (pressure detection means) when the pressure is changed by the peristaltic pump 28 (pressure changing means) and the detection value (output voltage) of the load sensor 18 (displacement detecting means).

Based on the calibration curve obtained by the calibration curve acquiring means 26, the calibration of the load sensor 18 and the pressure calculating means 20 is performed and the calibrated load sensor 18 and pressure calculating means 20 detect the blood removal pressure at the time of the dialysis treatment at the time of the blood purification treatment). That is, the calibrated load sensor 18 (displacement detecting means) and pressure calculating means 20 can calculate the blood removal pressure which is the pressure in the liquid flow route from the tip of the arterial blood circuit 1 to the peristaltically-actuated tube 1a in the extracorporeally circulating process of the blood at the time of the blood purification treatment.

According to the present embodiment, the pressure changing means is the peristaltic pump 28 of the liquid level adjusting means 27 which is caused to rotate at the time of the blood purification treatment and the pressure detection means is the venous pressure sensor 29 which detects the pressure (venous pressure) at the time of the blood purification treatment. Therefore, in addition to the effects of the above embodiments, it is possible to divert the liquid level adjusting means 27 utilized at the time of the blood purification treatment as components of the calibration means. As described in the above embodiments, the pressure changing means or the pressure detection means may use new means separate from the means utilized at the time of the blood purification treatment.

Here, each of the pressure changing means according to the first to fourth embodiments described above causes the flow route formed and closed by the closed flow route forming means to have the negative pressure such that the pressure is changed. However, as in the fifth embodiment, the pressure changing means may cause the flow route formed and closed by the closed flow route forming means to have the negative pressure and the positive pressure such that the pressure is changed. In this case, an example in which the closed flow route has the negative pressure at the time of the calibration can be the same as in the first to fifth embodiments described above and an example in which the closed flow route has the positive pressure at the time of the calibration is as illustrated in FIGS. 13 and 14.

In a case as illustrated in FIG. 13, for example, the electromagnetic valves V1 to V9 are selectively electrified by the control means that controls the present dialysis apparatus (blood purification apparatus) such that, as illustrated in the drawing, the closed circuit is formed in a state in which the electromagnetic valves V2, V7, and V9 are in a state of being open and the other electromagnetic valves V1, V3 to V6, and V8 are in a state of being closed. The positive pressure is imparted to the load sensor 18 as the displacement detecting means and the liquid pressure measuring means 25 as the pressure detection means by causing the blood pump 4 to reversely rotate such that the pressure is changed.

The calibration curve acquiring means 26 can produce and acquire the calibration curve, with which the load sensor 18 and the pressure calculating means 20 are calibrated, by a relationship between the pressure change (pressure difference before and after the rotation of the blood pump 4) detected by the liquid pressure measuring means 25 (pressure detection means) when the pressure is changed by the blood pump 4 (pressure changing means) and the detection value (output voltage) of the load sensor 18 (displacement detecting means). Based on the calibration curve obtained by the calibration curve acquiring means 26, the calibration of the load sensor 18 and the pressure calculating means 20 is performed.

In a case as illustrated in FIG. 14, the dialysate supplying line is not connected to the applied blood circuit. For example, the electromagnetic valves V1 to V8 are selectively electrified by the control means that controls the present dialysis apparatus (blood purification apparatus) such that, as illustrated in the drawing, the closed circuit is formed in a state in which the electromagnetic valves V1, V2, V4, and V8 are in a state of being open and the other electromagnetic valves V3 and V5 to V7 are in a state of being closed. The duplex pump 21 is caused to rotate and thus, the dialysate in the dialysate guiding-in line L1 is subjected to back-filtration (filtration from the dialysate flow route to the blood flow route) and is guided to the blood circuit side. The positive pressure is imparted to the load sensor 18 as the displacement detecting means and the venous pressure sensor 7 as the pressure detection means such that the pressure is changed.

The calibration curve acquiring means 26 can produce and acquire the calibration curve, with which the load sensor 18 and the pressure calculating means 20 are calibrated, by a relationship between the pressure change (pressure difference before and after the rotation of the blood pump 4) detected by the venous pressure sensor 7 (pressure detection means) when the pressure is changed by the duplex pump 21 (pressure changing means) and the detection value (output voltage) of the load sensor 18 (displacement detecting means). Based on the calibration curve obtained by the calibration curve acquiring means 26, the calibration of the load sensor 18 and the pressure calculating means 20 is performed.

According to illustration in FIG. 13 and FIG. 14, the pressure changing means causes the flow route formed and closed by the closed flaw route forming means to have the negative pressure such that the pressure is changed. Therefore, it is possible to reproduce the same conditions as in a case where the negative pressure is generated at the time of the blood removal in the blood purification treatment and in a case where the blood pump 4 is caused to reversely rotate in the blood returning or the like and it is possible to perform the calibration of the load sensor 18 (displacement detecting means) and the pressure calculating means 20 with higher accuracy.

Next, a sixth embodiment of the present invention will be described.

Similar to the above embodiments, the pressure detection device according to the present embodiment detects the pressure in the blood circuit (specifically, on the upstream side from the portion on which the blood pump, is disposed) which performs the blood purification treatment (for example, hemodialysis treatment) by the extracorporeal circulation of the blood of the patient. The applied blood circuit and the dialysis apparatus main body are configured to be the same as described in the above embodiments. The same reference signs are attached to the same components as those in the above embodiments and detailed description thereof is omitted.

As illustrated in FIGS. 15 and 16, a blood pump 4' (peristaltic pump) according to the present embodiment is configured mainly to have the stator 8, the rotor 9 that can rotate in the stator 8, the roller 10 (peristalsis section) formed in the rotor 9, the pair of upper and lower guide pins 11, upstream-side grasping means 12', the downstream-side grasping means 13, and a pressure transducer 30 as the displacement detecting means. The same reference numbers are attached to the same components as those in the above embodiments in the blood pump 4' and the description thereof is omitted.

The upstream-side grasping means 12' grasps the upstream side (a portion to which the tip side of the arterial blood circuit 1 is connected) of the peristaltically-actuated tube 1a mounted on the mounting concave section 8a of the stator 8 in the blood pump 4'. As illustrated in FIG. 16, the upstream-side grasping means 12' includes the grasping piece 14 that presses the peristaltically-actuated tube 1a in the radial direction so as to grasp the peristaltically-actuated tube 1a and the torsion spring 15 (biasing means) that biases the grasping piece 14 to the peristaltically-actuated tube 1a side.

The pressure transducer 30 as the displacement detecting means can detect displacement in the radial direction of a portion of the peristaltically-actuated tube 1a which is grasped by the upstream-side grasping means 12'. According to the present embodiment, the pressure transducer 30 is provided on a portion facing the grasping piece 14 with the peristaltically-actuated tube 1a interposed therebetween, detects pressure which is imparted on the side surface of the peristaltically-actuated tube 1a pressed by the grasping piece 14, and detects displacement of the peristaltically-actuated tube 1a in the radial direction based on the detected pressure.

That is, when the blood is collected from the patient and is caused to flow in the arterial blood circuit 1, pressure of the liquid in the peristaltically-actuated tube 1a is lowered when the negative pressure is generated between the tip of the arterial blood circuit 1 and the blood pump 4' and the portion of the penstaltically-actuated tube 1a which is grasped by the upstream-side grasping means 12' tends to be displaced (the diameter becomes small) in the radial direction. Therefore, the contact area with the pressure transducer 30 becomes small such that the pressure detected by the pressure transducer 30 is lowered. The pressure reduction is detected and thereby, it is possible to detect that the negative pressure is generated in the arterial blood circuit 1.

Similar to the above embodiments, the pressure transducer 30 (displacement detecting means) according to the present embodiment is electrically connected to the pressure calculating means 20 by extending a wire therein or the like. The pressure calculating means 20 is, for example, a microcomputer or the like disposed in the dialysis apparatus main body such that the pressure calculating means 20 is configured to calculate pressure in the arterial blood circuit 1 (liquid flow route) based on the displacement of the peristaltically-actuated tube 1a in the radial direction which is detected by the pressure transducer 30 (displacement detecting means).

Similar to the first to fifth embodiments, the calibration means is provided, which includes the closed flow route forming means, the pressure changing means, the pressure detection means, and the calibration curve acquiring means 26 and is configured to calibrate the pressure transducer 30 (displacement detecting means) and the pressure calculating means 20. In the closed flow route forming means, the pressure changing means, or the pressure detection means, it is possible to have the same or similar function as the above embodiments.

According to the present embodiment, the upstream-side grasping means 12' includes the grasping piece 14 that presses the peristaltically-actuated tube 1a in the radial direction so as to grasp the peristaltically-actuated tube 1a and the torsion spring 15 (biasing means) that biases the grasping piece 14 to the peristaltically-actuated tube 1*a* side. The pressure transducer 30 as the displacement detecting means is provided on the portion facing the grasping piece 14 with the peristaltically-actuated tube 1*a* interposed therebetween, detects pressure which is imparted on the side surface of the peristaltically-actuated tube 1*a* pressed by the grasping piece 14, and detects displacement of the peristaltically-actuated tube 1*a* in the radial direction based on the detected pressure. Therefore, it is possible for the displacement detecting means (pressure transducer 30) in the blood pump 4' to fulfill both a function of receiving a pressing force against the peristaltically-actuated tube 1*a* and a function of detecting the pressure of the arterial blood circuit 1.

As is clear from the present embodiment, a scope of the present invention is not limited to a case where the displacement of the peristaltically-actuated tube in the radial direction at a portion of the liquid flow route, at which the displacement detecting means is positioned, actually occurs, as in the embodiments described above, but a case where, for example, the grasping means confines and interposes both sides of the tube such that the side surfaces are confined so as not to be displaced, although a force to make displacement in the radial direction acts on the side surfaces, is also included in the scope. That is, according to the invention, it is sufficient for the displacement of the peristaltically-actuated tube 1*a* in the radial direction to be detected directly or indirectly and, similar to the present embodiment, the displacement produced when there is no confinement may be detected.

As above, the present embodiment is described, however, the present invention is not limited thereto. For example, instead of the load sensor 18 and the pressure transducer 30, other forms of displacement detecting means may be used and it is possible to use other forms of blood circuits (including other forms of blood purifiers instead of the dialyzer 3), dialysis apparatus main bodies (including chamber systems or the like instead of the duplex pump 21), or the like. The applied peristaltic pump may be, for example, a substitution pump or the like, other than the blood pump.

As long as the closed flow route forming means in the calibration means is means which can form a flow route that is closed and includes the portion of the peristaltically-actuated tube 1*a* at which the displacement detecting means is disposed, other forms of means (means which closes the flow route manually, or the like) may be used. Further, as long as the pressure changing means in the calibration means is means which can arbitrarily change the pressure in the flow route formed and closed by the closed flow route forming means, other forms of means (not limited to the case where the pump used at the time of the blood purification treatment is diverted) may be used. Further, as long as the pressure detection means in the calibration means is means which can detect the pressure change in the flow route formed and closed by the closed flow route forming means, other forms of means (not limited to the case where the sensor used at the time of blood purification treatment is diverted) may be used.

INDUSTRIAL APPLICABILITY

According to the present invention, as long as a pressure detection device of a liquid flow route includes displacement detecting means that detects displacement of a peristaltically-actuated tube in the radial direction, pressure calculating means that can calculate pressure of a liquid flow route based on the displacement of the peristaltically-actuated tube in the radial direction which is detected by the displacement detecting means, and calibration means that calibrates the displacement detecting means and the pressure calculating means, in which the calibration means has closed flow route forming means that can form a flow route which is closed and includes a portion in the peristaltically-actuated tube at which the displacement detecting means is disposed, pressure changing means that can arbitrarily change the pressure in the flow route formed and closed by the closed flow route forming means, pressure detection means that can detect pressure change in the flow route formed and closed by the closed flow route forming means, and calibration curve acquiring means that can produce and acquire a calibration curve, with which the displacement detecting means and pressure calculating means are calibrated, by a relationship between the pressure change detected by the pressure detection means when the pressure is changed by the pressure changing means and a detection value of the displacement detecting means, it is possible to apply the invention to the pressure detection device that has a different external shape or has another additional function.

REFERENCE SIGNS LIST a. arterial blood circuit (liquid flow route)
1*a* peristaltically-actuated tube
2 venous blood circuit
3 dialyzer (blood purifier)
4, 4' blood pump (peristaltic pump)
5 arterial air trap chamber
6 venous air trap chamber
7 venous pressure sensor
8 stator
9 rotor
10 roller (peristalsis section)
11 guide pin
12, 12' upstream-side grasping means
13 downstream-side grasping means
14 grasping piece
15 torsion spring (biasing means)
16 grasping piece
17 torsion spring
18 load sensor (displacement detecting means)
19 collecting port
20 pressure calculating means
21 duplex pump
22 ultrafiltration pump
23 filter
24 filter
25 liquid pressure measuring means (dialysate pressure sensor)
26 calibration curve acquiring means
27 liquid level adjusting means
28 peristaltic pump
29 venous pressure sensor
30 pressure transducer (displacement detecting means)
V1 to V9 electromagnetic valve (closed flow route forming means)

The invention claimed is:
1. A pressure detection device of a liquid flow route that detects pressure of the liquid flow route configured of a flexible tube, a portion of which is connected to a peristaltically-actuated tube that causes an internal liquid to flow by being compressed in a radial direction and by being peristaltically actuated in a longitudinal direction by a peristalsis section of a peristaltic pump, and which enables a predetermined liquid to be circulated, the pressure detection device comprising:
displacement detecting means that detects displacement of the peristaltically-actuated tube in the radial direction;
pressure calculating means that is able to calculate pressure of the liquid flow route based on the displacement of the peristaltically-actuated tube in the radial direction which is detected by the displacement detecting means; and
calibration means that calibrates the displacement detecting means and the pressure calculating means,
wherein the calibration means includes
closed flow route forming means that is able to form a flow route which is closed and includes a portion in the peristaltically-actuated tube at which the displacement detecting means is disposed,
pressure changing means that is able to arbitrarily change the pressure in the flow route formed and closed by the closed flow route forming means,
pressure detection means that is able to detect pressure change in the flow route formed and closed by the closed flow route forming means, and
calibration curve acquiring means that is able to produce and acquire a calibration curve with which the displacement detecting means and pressure calculating means are calibrated by a relationship between the pressure change detected by the pressure detection means when the pressure is changed by the pressure changing means and a detection value of the displacement detecting means.

2. The pressure detection device of a liquid flow route according to claim 1,
wherein the peristaltically-actuated tube is connected to an intermediate portion of an arterial blood circuit that extracorporeally circulates blood of a patient at time of a blood purification treatment, the peristaltic pump is a blood pump that causes the blood in the arterial blood circuit to flow, and blood removal pressure in the liquid flow route from a tip of the arterial blood circuit to the peristaltically-actuated tube is caused to be calculated by the displacement detecting means and the pressure calculating means in an extracorporeally circulating process of the blood at the time of the blood purification treatment and a blood returning process.

3. The pressure detection device of a liquid flow route according to claim 2,
wherein the pressure changing means is a pump which is rotated at the time of the blood purification treatment and the pressure detection means is a sensor which detects pressure at the time of the blood purification treatment.

4. The pressure detection device of a liquid flow route according to claim 2,
wherein calibration of the displacement detecting means and the pressure calculating means is performed for each blood purification treatment by the calibration means.

5. The pressure detection device of a liquid flow route according to claim 2, wherein the pressure changing means generates a negative pressure in the flow route formed and closed by the closed flow route forming means so as to change pressure in the flow route.

6. The pressure detection device of a liquid flow route according to claim 2, wherein the pressure changing means generates a negative pressure and a positive pressure in the flow route formed and closed by the closed flow route forming means so as to change the pressure in the flow route.

7. The pressure detection device of a liquid flow route according to claim 1, wherein the calibration curve acquiring means is able to produce and acquire a calibration curve with a pressure difference based on a difference between dispositional heights of the displacement detecting means and the pressure detection means taken into account.

8. The pressure detection device of a liquid flow route according to claim 2, further comprising:
notifying means that is able to perform notification under a condition that the blood removal pressure calculated by the displacement detecting means and the pressure detection means exceeds a preset value.

9. The pressure detection device of a liquid flow route according to claim 1, wherein the peristaltic pump includes grasping means that grasps the peristaltically-actuated tube mounted on the peristaltic pump and the displacement detecting means is able to detect displacement in the radial direction of a portion grasped by the grasping means.

10. The pressure detection device of a liquid flow route according to claim 9, wherein the grasping means has a grasping piece that presses the peristaltically-actuated tube in the radial direction so as to grasp the peristaltically-actuated tube and biasing means that biases the grasping piece against the peristaltically-actuated tube and the displacement detecting means detects a load applied on a fixed end side of the biasing means and detects displacement of the peristaltically-actuated tube in the radial direction based on the detected load.

11. The pressure detection device of a liquid flow route according to claim 9, wherein the grasping means has a grasping piece that presses the peristaltically-actuated tube in the radial direction so as to grasp the peristaltically-actuated tube and biasing means that biases the grasping piece against the peristaltically-actuated tube and the displacement detecting means is provided on a portion facing the grasping piece with the peristaltically-actuated tube interposed therebetween, detects pressure which is imparted on a side surface of the peristaltically-actuated tube pressed by the grasping piece, and detects displacement of the peristaltically-actuated tube in the radial direction based on the detected pressure.

12. A peristaltic pump comprising:
the pressure detection device of a liquid flow route according to claim 1.

13. A blood purification apparatus comprising:
the peristaltic pump according to claim 12.

14. The pressure detection device of a liquid flow route according to claim 3, wherein calibration of the displacement detecting means and the pressure calculating means is performed for each blood purification treatment by the calibration means.

15. The pressure detection device of a liquid flow route according to claim 3, wherein the pressure changing means generates a negative pressure in the flow route formed and closed by the closed flow route forming means so as to change pressure in the flow route.

16. The pressure detection device of a liquid flow route according to claim 4, wherein the pressure changing means generates a negative pressure in the flow route formed and closed by the closed flow route forming means so as to change pressure in the flow route.

17. The pressure detection device of a liquid flow route according to claim 3, wherein the pressure changing means generates a negative pressure and a positive pressure in the flow route formed and closed by the closed flow route forming means so as to change the pressure in the flow route.

18. The pressure detection device of a liquid flow route according to claim 4, wherein the pressure changing means generates a negative pressure and a positive pressure in the flow route formed and closed by the closed flow route forming means so as to change the pressure in the flow route.

19. The pressure detection device of a liquid flow route according to claim 2, wherein the calibration curve acquiring means is able to produce and acquire a calibration curve with a pressure difference based on a difference between dispositional heights of the displacement detecting means and the pressure detection means taken into account.

20. The pressure detection device of a liquid flow route according to claim 3, wherein the calibration curve acquiring means is able to produce and acquire a calibration curve with a pressure difference based on a difference between dispositional heights of the displacement detecting means and the pressure detection means taken into account.

* * * * *